United States Patent
Yager et al.

(10) Patent No.: US 12,263,193 B2
(45) Date of Patent: Apr. 1, 2025

(54) SYSTEM AND METHOD FOR REMOVING UREMIC TOXINS FROM A PATIENT'S BODY

(71) Applicant: University of Washington, Seattle, WA (US)

(72) Inventors: Paul Yager, Seattle, WA (US); Jonathan Himmelfarb, Seattle, WA (US); Mari-Karoliina Henriikka Winkler, Seattle, WA (US); Erin Heiniger, Seattle, WA (US); Sujatha Kumar, Seattle, WA (US); David Stahl, Seattle, WA (US); Bruce Godfrey, Seattle, WA (US)

(73) Assignee: University of Washington, Seattle, WA (US)

( * ) Notice: Subject to any disclaimer, the term of this patent is extended or adjusted under 35 U.S.C. 154(b) by 877 days.

(21) Appl. No.: 17/284,759

(22) PCT Filed: Oct. 14, 2019

(86) PCT No.: PCT/US2019/056119
§ 371 (c)(1),
(2) Date: Apr. 12, 2021

(87) PCT Pub. No.: WO2020/077338
PCT Pub. Date: Apr. 16, 2020

(65) Prior Publication Data
US 2022/0000938 A1    Jan. 6, 2022

Related U.S. Application Data

(60) Provisional application No. 62/744,966, filed on Oct. 12, 2018.

(51) Int. Cl.
*A61K 35/74*    (2015.01)
*A61K 9/16*    (2006.01)

(52) U.S. Cl.
CPC ............ *A61K 35/74* (2013.01); *A61K 9/1652* (2013.01); *A61K 9/1658* (2013.01); *A61K 9/1682* (2013.01)

(58) Field of Classification Search
None
See application file for complete search history.

(56) References Cited

U.S. PATENT DOCUMENTS

| | | | |
|---|---|---|---|
| 6,217,859 B1 | 4/2001 | Chang et al. | |
| 6,861,064 B1 * | 3/2005 | Laakso | B01J 13/18 427/213.3 |

(Continued)

FOREIGN PATENT DOCUMENTS

| | | |
|---|---|---|
| CN | 1509144 A | 6/2004 |
| CN | 102864088 | 1/2013 |

(Continued)

OTHER PUBLICATIONS

Papadimitriou, Sofia; et al; "Chitosan-g-PEG nanoparticles ionically crosslinked with poly(glutamic acid) and tripolyphosphate as protein delivery systems" International Journal of Pharmaceutics, 430, 318-327, 2012 (Year: 2012).*

(Continued)

*Primary Examiner* — David W Berke-Schlessel
(74) *Attorney, Agent, or Firm* — Christensen O'Connor Johnson Kindness PLLC

(57) ABSTRACT

Compositions and method for reducing the concentration of uremic toxins in the body of a patient suffering from some degree of kidney failure are disclosed. The methods can be used to delay the need for conventional dialysis treatment or as an adjunct therapy to reduce the frequency of dialysis sessions, and in some instances, as an alternative to such dialysis sessions.

14 Claims, 10 Drawing Sheets

(56) References Cited

U.S. PATENT DOCUMENTS

| | | | |
|---|---|---|---|
| 7,597,808 | B2 | 10/2009 | Shiotani |
| 8,227,238 | B2 | 7/2012 | Abe |
| 8,293,109 | B2 | 10/2012 | Kimura |
| 9,212,358 | B2 | 12/2015 | Razavi-Shirazi |
| 10,202,567 | B2 | 2/2019 | Stolaroff |
| 10,894,732 | B2 | 1/2021 | Novak |
| 2001/0051150 | A1 | 12/2001 | Ranganathan et al. |
| 2002/0187134 | A1 | 12/2002 | Ranganathan |
| 2004/0209361 | A1 | 10/2004 | Hemperly |
| 2004/0234962 | A1 | 11/2004 | Alarcon |
| 2005/0123529 | A1 | 6/2005 | O'Loughlin |
| 2007/0205149 | A1 | 9/2007 | Jones |
| 2008/0051696 | A1 | 2/2008 | Curtin |
| 2008/0264858 | A1 | 10/2008 | Stamets |
| 2009/0143463 | A1 | 6/2009 | Takenaka |
| 2010/0114012 | A1 | 5/2010 | Sandford |
| 2010/0317085 | A1 | 12/2010 | Boedicker |
| 2012/0177622 | A1 | 7/2012 | Suzuki |
| 2016/0030890 | A1 | 2/2016 | Lee |
| 2016/0031766 | A1 | 2/2016 | Bezbaruah |
| 2016/0051600 | A1 | 2/2016 | Martín Del Campo López |
| 2016/0144094 | A1 | 5/2016 | Margolin |
| 2017/0258857 | A1 | 9/2017 | Philipp |
| 2017/0355979 | A1 | 12/2017 | Bae |
| 2018/0021386 | A1 | 1/2018 | Shum |
| 2018/0021452 | A1 | 1/2018 | Huang |
| 2018/0084805 | A1 | 3/2018 | Fang |
| 2018/0289755 | A1 | 10/2018 | Al-Furaih |
| 2019/0218497 | A1 | 7/2019 | Boedicker |
| 2019/0375662 | A1 | 12/2019 | Novak |
| 2020/0255818 | A1 | 8/2020 | Knipe |
| 2024/0076221 | A1 | 3/2024 | Redcorn et al. |

FOREIGN PATENT DOCUMENTS

| | | |
|---|---|---|
| CN | 102864088 A | 1/2013 |
| CN | 103667124 | 3/2014 |
| CN | 103667124 A | 3/2014 |
| CN | 106222158 | 12/2016 |
| CN | 106222158 A | 12/2016 |
| CN | 106830563 A | 6/2017 |
| CN | 107156587 | 9/2017 |
| CN | 107156587 A | 9/2017 |
| CN | 107324616 A | 11/2017 |
| CN | 109464225 | 3/2019 |
| CN | 109464225 A | 3/2019 |
| CN | 109496234 | 3/2019 |
| CN | 109496234 A | 3/2019 |
| CN | 109734174 A | 5/2019 |
| ES | 2368401 | 11/2011 |
| ES | 2368401 A1 | 11/2011 |
| JP | 10180282 A | 7/1998 |
| JP | 3361570 B2 | 1/2003 |
| JP | 2004033808 A | 2/2004 |
| JP | 2004533442 | 11/2004 |
| JP | 2007507526 | 3/2007 |
| JP | 2008018153 | 1/2008 |
| JP | 2014199432 | 10/2014 |
| JP | 2014199432 A | 10/2014 |
| TW | 201427673 | 7/2014 |
| TW | 201427673 A | 7/2014 |
| WO | 02091833 A1 | 11/2002 |
| WO | 2002091833 | 11/2002 |
| WO | 2002091833 A1 | 11/2002 |
| WO | 2003088984 | 10/2003 |
| WO | 2003088984 A1 | 10/2003 |
| WO | 2004094625 A1 | 11/2004 |
| WO | 2014033638 | 3/2014 |
| WO | 2015019307 | 2/2015 |
| WO | 2015019307 A1 | 2/2015 |
| WO | 2017136561 A1 | 8/2017 |
| WO | 2018017845 A1 | 1/2018 |
| WO | 2019117645 | 6/2019 |
| WO | 2019117645 A1 | 6/2019 |

OTHER PUBLICATIONS

Jo, Yun-Suk; et al; "Encapsulation of Bovine Serum Albumin in Temperature-Programmed "Shell-in-Shell" Structures" Macromolecule Rapid Communications, 24, 957-962, 2003 (Year: 2003).*

Lim, Trisna; "Microcapsules immobilizing activated charcoal and metabolically induced Lactobacillus acidophilus cells as potential oral renal failure therapy formulation" Masters Thesis, McGill University, Feb. 2006 (Year: 2006).*

Qiu, Bo; et al; "A hydrogel prepared by in situ cross-linking of a thiol-containing poly(ethylene glycol)-based copolymer: a new biomaterial for protein drug delivery" Biomaterials, 24, 11-18, 2003 (Year: 2003).*

Quellec, P; et al; "Protein encapsulation within polyethylene glycol-coated nanospheres" Journal of Biomedical Materials Research, 42, 42-54, 1998 (Year: 1998).*

Coussa, R.G. et al. Microencapsulated *Saccharomyces cerevisiae* Columm Bioreactor for Potential Use in Renal Failure Uremia, Artificial Cells, Blood Substitutes, and Biotechnology, 40;1-2 (2012) 103-112.

Takayama, F. et al. Bifidobacterium in Gastro-Resistant Seamless Capsule Reduces Serum Levels of Indoxyl Sulfate in Patients on Hemodialysis, American Journal of Kidney Diseases, vol. 41, No. 1, Suppl 1 Mar. 2003: pp. S142-S145.

International Prelimininary Report on Patentability mailed Apr. 8, 2021, issued in corresponding International Application No. PCT/US2019/056119, filed on Oct. 14, 2019, 6 pages.

International Search Report and Written Opinion mailed Jan. 2, 2020, issued in corresponding International Application No. PCT/US2019/056119, filed on Oct. 14, 2019, 8 pages.

International Prelimininary Report on Patentability mailed Apr. 19, 2022, issued in corresponding International Application No. PCT/US2020/055402, filed on Oct. 13, 2020, 1 pages.

International Search Report and Written Opinion mailed Feb. 10, 2021, issued in corresponding International Application No. PCT/US2020/055402, filed on Oct. 13, 2020, 8 pages.

Agler, Matthew T., et al. "Waste to bioproduct conversion with undefined mixed cultures: the carboxylate platform." Trends in biotechnology 29.2 (2011): 70-78.

Ahn, Young-Ho. "Sustainable nitrogen elimination biotechnologies: a review." Process Biochemistry 41.8 (2006): 1709-1721.

Ali, Muhammad, et al. "Rapid and successful start-up of anammox process by immobilizing the minimal quantity of biomass in PVA-SA gel beads." Water research 79 (2015): 147-157.

Alisawi, Hussein Abed Obaid. "Performance of wastewater treatment during variable temperature." Applied Water Science 10.89 (2020): 1-6.

Bae, Hyokwan, et al. "Core-shell structured poly (vinyl alcohol)/sodium alginate bead for single-stage autotrophic nitrogen removal." Chemical Engineering Journal 322 (2017): 408-416.

Beyenal, H., and A. Tanyolac. "The calculation of simultaneous effective diffusion coefficients of the substrates in a fluidized bed biofilm reactor." Water Science and Technology 29.10-11 (1994): 463-470.

Blackburne, Richard, Zhiguo Yuan, and Jürg Keller. "Partial nitrification to nitrite using low dissolved oxygen concentration as the main selection factor." Biodegradation 19.2 (2008): 303-312.

Boušková, Alžběta, et al. "Three examples of nitrogen removal from industrial wastewater using Lentikats Biotechnology." Desalination 280.1-3 (2011): 191-196.

Bulut, Emine, and Oya Şanli. "Novel ionically crosslinked acrylamide-grafted poly (vinyl alcohol)/sodium alginate/sodium carboxymethyl cellulose pH-sensitive microspheres for delivery of Alzheimer's drug donepezil hydrochloride: Preparation and optimization of release conditions." Artificial Cells, Nanomedicine, and Biotechnology 44.2 (2016): 431-442.

Cao, Guo-min, et al. "Characterization of nitrifying and denitrifying bacteria coimmobilized in PVA and kinetics model of biological nitrogen removal by coimmobilized cells." Enzyme and Microbial Technology 30.1 (2002): 49-55.

Cao, Yeshi, Mark van Loosdrecht, and Glen T. Daigger. "Mainstream partial nitritation-anammox in municipal wastewater treat-

(56) References Cited

OTHER PUBLICATIONS ment: status, bottlenecks, and further studies." Applied microbiology and biotechnology 101.4 (2017): 1365-1383.
Carvajal-Arroyo, José M., et al. "Granular fermentation enables high rate caproic acid production from solid-free thin stillage." Green Chemistry 21.6 (2019): 1330-1339.
Chaitali, Mandal, et al. "Productivity improvement in xanthan gum fermentation using multiple substrate optimization." Biotechnology progress 19.4 (2003): 1190-1198.
Chen, Guanghui, et al. "Anaerobic ammonium oxidation (ANAMMOX) sludge immobilized by waterborne polyurethane and its nitrogen removal performance—a lab scale study." Rsc Advances 5.32 (2015): 25372-25381.
Chen, Yan, et al. "Preliminary study of shortcut nitrification and denitrification using immobilized of mixed activated sludge and denitrifying sludge." Procedia Environmental Sciences 11 (2011): 1171-1176.
Chiu, Z. C., et al. "Diffusivity of oxygen in aerobic granules." Biotechnology and bioengineering 94.3 (2006): 505-513.
De Almeida Fernandes, Luyara, et al. "Effect of temperature on microbial diversity and nitrogen removal performance of an anammox reactor treating anaerobically pretreated municipal wastewater." Bioresource technology 258 (2018): 208-219.
De Kreuk, M. K., N. Kishida, and M. C. M. Van Loosdrecht. "Aerobic granular sludge-state of the art." Water Science and Technology 55.8-9 (2007): 75-81.
De Smet, Stefaan, et al. "Gut antibacterial effects of C7 and C9 carboxylic acids in the diet of piglets." Journal of Animal Science 94.suppl_3 (2016): 54-57.
Desai, N. P., et al. "Interpenetrating polymer networks of alginate and polyethylene glycol for encapsulation of islets of Langerhans." Journal of microencapsulation 17.6 (2000): 677-690.
Ding, Shuang, et al. "Ecological characteristics of anaerobic ammonia oxidizing bacteria." Applied microbiology and biotechnology 97.5 (2013): 1841-1849.
Dolejš, Igor, et al. "Nitrogen removal by co-immobilized anammox and ammonia-oxidizing bacteria in wastewater treatment." Catalysts 9.523 (2019): 1-8.
French, Elizabeth, et al. "Ecophysiological characterization of ammonia-oxidizing archaea and bacteria from freshwater." Applied and Environmental Microbiology 78.16 (2012): 5773-5780.
Furukawa, Kenji, et al. "Innovative treatment system for digester liquor using anammox process." Bioresource Technology 100.22 (2009): 5437-5443.
Fux, Christian, et al. "Biological treatment of ammonium-rich wastewater by partial nitrification and subsequent anaerobic ammonium oxidation (anammox) in a pilot plant." Journal of biotechnology 99.3 (2002): 295-306.
Gong, Jian Ping. "Friction and lubrication of hydrogels—its richness and complexity." Soft matter 2.7 (2006): 544-552.
Grant, Shannon, and Kwan-Chow Lin. "Effects of temperature and organic loading on the performance of upflow anaerobic sludge blanket reactors." Canadian journal of civil engineering 22.1 (1995): 143-149.
Guo, Jianhua, et al. "Long-term effect of dissolved oxygen on partial nitrification performance and microbial community structure." Bioresource technology 100.11 (2009): 2796-2802.
Harroff, Lauren A., et al. "Inactivation of Ascaris eggs in human fecal material through in situ production of carboxylic acids." Environmental Science & Technology 51.17 (2017): 9729-9738.
Hellinga, C. S. A. A. J. C., et al. "The Sharon process: an innovative method for nitrogen removal from ammonium-rich waste water." Water science and technology 37.9 (1998): 135-142.
Holenda, B., et al. "Dissolved oxygen control of the activated sludge wastewater treatment process using model predictive control." Computers & Chemical Engineering 32.6 (2008): 1270-1278.
Holst, Olle, Hans Lundbäck, and Bo Mattiasson. "Hydrogen peroxide as an oxygen source for immobilized Gluconobacter oxydans converting glycerol to dihydroxyacetone." Applied microbiology and biotechnology 22.6 (1985): 383-388.

Ibrahim, M., and H. G. Schlegel. "Oxygen supply to bacterial suspensions of high cell densities by hydrogen peroxide." Biotechnology and Bioengineering 22.9 (1980): 1877-1894.
Isaka, Kazuichi, et al. "Nitrogen removal performance using anaerobic ammonium oxidation at low temperatures." FEMS microbiology letters 282.1 (2008): 32-38.
Isaka, Kazuichi, Tatsuo Sumino, and Satoshi Tsuneda. "Ammonium removal performance of anaerobic ammonium-oxidizing bacteria immobilized in polyethylene glycol gel carrier." Applied microbiology and biotechnology 76.6 (2007): 1457-1465.
Isaka, Kazuichi, et al. "Complete autotrophic denitrification in a single reactor using nitritation and anammox gel carriers." Bioresource technology 147 (2013): 96-101.
Isaka, Kazuichi, et al. "First full-scale nitritation-anammox plant using gel entrapment technology for ammonia plant effluent." Biochemical engineering journal 122 (2017): 115-122.
Isaka, Kazuichi, et al. "Growth characteristic of anaerobic ammonium-oxidizing bacteria in an anaerobic biological filtrated reactor." Applied microbiology and biotechnology 70.1 (2006): 47-52.
Jianlong, Wang, and Yang Ning. "Partial nitrification under limited dissolved oxygen conditions." Process Biochemistry 39.10 (2004): 1223-1229.
Jo, Yeadam, et al. "Treatment of low-strength ammonia wastewater by single-stage partial nitritation and anammox using upflow dual-bed gel-carrier reactor (UDGR)." Bioresource technology 304 (2020): 123023.
Johnston, Trevor G., et al. "Compartmentalized microbes and co-cultures in hydrogels for on-demand bioproduction and preservation." Nature communications 11.563 (2020): 1-11.
Jones, Peter, and A. Suggett. "The catalase-hydrogen peroxide system. Kinetics of catalatic action at high substrate concentrations." Biochemical Journal 110.4 (1968): 617-620.
Kalvelage, Tim, et al. "Oxygen sensitivity of anammox and coupled N-cycle processes in oxygen minimum zones." PloS one 6.12 (2011): e29299.
Kane, William J., J. Ledlie Klosky, and C. James Martel. "Portable wastewater treatment." Water environment & technology 13.3 (2001): 44-48.
Khanh, Dophuong, et al. "Effect of temperature on low-strength wastewater treatment by UASB reactor using poly (vinyl alcohol)-gel carrier." Bioresource technology 102.24 (2011): 11147-11154.
Kim, Jeonghwan, et al. "Anaerobic fluidized bed membrane bioreactor for wastewater treatment." Environmental science & technology 45.2 (2011): 576-581.
Notice of First Office Action issued on Feb. 22, 2024 in corresponding Chinese Patent Application No. 201980067231.5 filed Oct. 14, 2019, 16 pages total (English machine translation included).
Winkler, Mari KH, et al. "Unravelling the reasons for disproportion in the ratio of AOB and NOB in aerobic granular sludge." Applied Microbiology and Biotechnology 94.6 (2012): 1657-1666.
Yeung, Timothy W., et al. "Microencapsulation of probiotics in hydrogel particles: enhancing *Lactococcus lactis* subsp. *cremoris* LM0230 viability using calcium alginate beads." Food & function 7.4 (2016): 1797-1804.
Cheng, Rong, Lin Lin, and Yongkui Zhang. "Hydrogen peroxide ($H2O2$) supply significantly improves xanthan gum production mediated by Xanthomonas campestris in vitro." Journal of Industrial Microbiology and Biotechnology 39.5 (2012).
De Man, A., van der Last, A.R.M., Lettinga, G., 1988. The use of EGSB and UASB anaerobic systems for low strength soluble and complex wastewaters at temperatures ranging from 8 to 30_C. In: Hal, E.R., Hobson, P.N. (Eds.), Proceeding of the Fifth International Symposium on Anaerobic Digestion, pp. 197-209.
Urban, Carolin, et al. "Production of drop-in fuels from biomass at high selectivity by combined microbial and electrochemical conversion." Energy & Environmental Science 10.10 (2017): 2231-2244.
Park, Hee-Deung, and Daniel R. Noguera. "Evaluating the effect of dissolved oxygen on ammonia-oxidizing bacterial communities in activated sludge." Water research 38.14-15 (2004): 3275-3286.
McKee, D. W. "Catalytic decomposition of hydrogen peroxide by metals and alloys of the platinum group." Journal of Catalysis 14.4 (1969): 355-364.

(56) References Cited

OTHER PUBLICATIONS

Melin, T., et al. "Membrane bioreactor technology for wastewater treatment and reuse." Desalination 187.1-3 (2006): 271-282.
Morris, Brandon EL, et al. "Microbial syntrophy: interaction for the common good." FEMS microbiology reviews 37.3 (2013): 384-406.
Omonijo, Faith A., et al. "Essential oils as alternatives to antibiotics in swine production." Animal Nutrition 4.2 (2018): 126-136.
Perez-Pinera, Pablo, et al. "Synthetic biology and microbioreactor platforms for programmable production of biologics at the point-of-care." Nature communications 7.12211 (2016): 1-10.
Picioreanu, Cristian, Mark CM van Loosdrecht, and Joseph J. Heijnen. "A new combined differential-discrete cellular automaton approach for biofilm modeling: Application for growth in gel beads." Biotechnology and bioengineering 57.6 (1998): 718-731.
Prosser, J.I. "Autotrophic nitrification in bacteria." Advances in microbial physiology 30 (1990): 125-181.
Qiao, Sen, et al. "Novel single-stage autotrophic nitrogen removal via co-immobilizing partial nitrifying and anammox biomass." Chemical engineering journal 230 (2013): 19-26.
Quan, Lai Minh, et al. "Reject water treatment by improvement of whole cell anammox entrapment using polyvinyl alcohol/alginate gel." Biodegradation 22.6 (2011): 1155-1167.
Rathore, Sweta, et al. "Microencapsulation of microbial cells." Journal of food engineering 116.2 (2013): 369-381.
Samarasinghe, S. A. P. L., et al. "Fabrication of bacteria environment cubes with dry lift-off fabrication process for enhanced nitrification." Plos one 11.11 (2016): e0165839.
Sarkar, Pritish, Kaushik Ghosh, and G. K. Suraishkumar. "High hydrogen peroxide concentration in the feed-zone affects bioreactor cell productivity with liquid phase oxygen supply strategy." Bioprocess and biosystems engineering 31.4 (2008): 357-367.
Schaffner, Manuel, et al. "3D printing of bacteria into functional complex materials." Science advances 3.12 (2017): eaao6804.
Sliekers, A. Olav, et al. "Canon and Anammox in a gas-lift reactor." FEMS microbiology letters 218.2 (2003): 339-344.
"Small Compressed Gas Cartridges." 2015. Transportation Security Administration. Feb. 12, 2015. https://www.tsa.gov/travel/security-screening/whatcanibring/items/small-compressed-gas-cartridges.
Stenstrom, Michael K., and Richard A. Poduska. "The effect of dissolved oxygen concentration on nitrification." Water research 14.6 (1980): 643-649.
Subramanian, S. Bala, et al. "Extracellular polymeric substances (EPS) producing bacterial strains of municipal wastewater sludge: isolation, molecular identification, EPS characterization and performance for sludge settling and dewatering." Water research 44.7 (2010): 2253-2266.
Sudarno, U., J. Winter, and C. Gallert. "Effect of varying salinity, temperature, ammonia and nitrous acid concentrations on nitrification of saline wastewater in fixed-bed reactors." Bioresource Technology 102.10 (2011): 5665-5673.
Sun, Yan, et al. "Diffusivity of oxygen into carriers entrapping whole cells." Biotechnology and bioengineering 34.1 (1989): 55-58.
Delgado Vela, Jeseth, et al. "Prospects for biological nitrogen removal from anaerobic effluents during mainstream wastewater treatment." Environmental Science & Technology Letters 2.9 (2015): 234-244.
Winkler, Mari KH, et al. "Segregation of biomass in cyclic anaerobic/aerobic granular sludge allows the enrichment of anaerobic ammonium oxidizing bacteria at low temperatures." Environmental Science & Technology 45.17 (2011): 7330-7337.
Cheng, Rong, Lin Lin, and Yongkui Zhang. "Hydrogen peroxide (H202) supply significantly improves xanthan gum production mediated by Xanthomonas campestris in vitro." Journal of Industrial Microbiology and Biotechnology 39.5 (2012).
Chai, Y. et al. Diffusion Coefficients in Intrahollow Calcium Alginate Microcapsules, J. Chem. Eng. Data 2004, 49, 475-478.
Prakash, S. et al. Growth and Survival of Renal Failure Rats that Received Oral Microencapsulated Genetically Engineered *E. Coli* Dh5 Cells for Urea Removal, Artificial Cells, Blood Substitutes, and Biotechnology, vol. 26, No. 1, 1998, 35-51.

Winkler, M. K., et al. "Factors influencing the density of aerobic granular sludge." Applied microbiology and biotechnology 97.16 (2013): 7459-7468.
Tamis, J., et al. "High-rate volatile fatty acid (VFA) production by a granular sludge process at low pH." Biotechnology and bioengineering 112.11 (2015): 2248-2255.
Meng, Jia, et al. "Effect of temperature on nitrogen removal and biological mechanism in an up-flow microaerobic sludge reactor treating wastewater rich in ammonium and lack in carbon source." Chemosphere 216 (2019): 186-194.
Soliman, Moomen, and Ahmed Eldyasti. "Ammonia-Oxidizing Bacteria (AOB): opportunities and applications—a review." Reviews in Environmental Science and Bio/Technology 17.2 (2018): 285-321.
Winkler, M-KH, et al. "Selective sludge removal in a segregated aerobic granular biomass system as a strategy to control PAO-GAO competition at high temperatures." Water research 45.11 (2011): 3291-3299.
Sultana, K. et al. Encapsulation of probiotic bacteria with alginate-starch and evaluation of survival in simulated gastrointestinal conditions and in yoghurt, International Journal of Food Microbiology 62 (2000) 47-55.
Bulut E. et al., "Novel ionically crosslinked acrylamide-grafted poly(vinyl alcohol)/sodium 1-3, 29-32. 39-41, 45-4 7 alginate/sodium carboxymethyl cellulose pH-sensitive microspheres for delivery of Alzheimer's drug donepezil hydrochloride: Preparation and optimization of release conditions", Artificial Cells, Nanomedicine, and Biotechnology, 2016, vol. 44, issue 2, pp. 431-442, retrieved from the Internet:< DOI: 10.3109/21691401.2014.962741 >; see entire document.
Combined International Search Report and Written Opinion received in International Application No. PCT/US2020/55402, filed Oct. 13, 2020; dated Mar. 11, 2021; 8 pages total.
Desai N. P. et al., "Interpenetrating polymer networks of alginate and polyethylene glycol for 1-3, 39-41, 45-47 encapsulation of islets of Langerhans", Journal of Microencapsulation, 2000, vol. 17, issue 6, pp. 677-690, retrieved from the Internet:< DOI: 10.1080/02652040050161675 >; see entire document, especially, p. 677-679.
C. Tomaro-Ducesneau et al., "Microencapsulation for the Therapeutic Delivery of Drugs, Live Mammalian and Bacterial Cells, and Other Biopharmaceutics: Current Status and Future Directions", Journal of Pharmaceutics, Dec. 4, 2012, pp. 1-19.
S. Prakash et al.,"Renal Failure Rats that Received Oral Microencapsulated Genetically Engineered *E. Coli* Dh5 Cells for Urea Removal", Artificial Cells, Blood Substitutes, and Immobilization Biotechnology., vol. 26, No. 1, Jan. 1, 1998, pp. 35-51.
B. Hamarat, "Alginate Beads Encapsulation Matrix for Urease and Polyethyleneglycol-Urease", Artificial Cells, Blood Substitutes, and Immobilization Biotechnology., vol. 35, No. 4, Jan. 1, 2007, pp. 457-465.
S. Abhishek et al. "Biopolymer matrix for nano-encapsulation of urease—A model protein and its application in urea detection", Journal of Colloid and Interface Science, Academic Press, Inc, US, vol. 490, Nov. 9, 2016, pp. 452-461.
Kimura, Yuya, Kazuichi Isaka, and Futaba Kazama. "Tolerance level of dissolved oxygen to feed into anaerobic ammonium oxidation (anammox) reactor." Journal of Water and Environment Technology 9.2 (2011): 169-178.
Könneke, Martin, et al. "Isolation of an autotrophic ammonia-oxidizing marine archaeon." Nature 437.22 (2005): 543-546.
Kucek, Leo A., et al. "Waste conversion into n-caprylate and n-caproate: resource recovery from wine lees using anaerobic reactor microbiomes and in-line extraction." Frontiers in microbiology 7 (2016): 1892.
Landreau, Matthieu, et al. "Effective nitrogen removal from ammonium-depleted wastewater by partial nitritation and anammox immobilized in granular and thin layer gel carriers." Water Research 183 (2020): 116078.
Landreau, Matthieu, et al. "Immobilization of active ammonia-oxidizing archaea in hydrogel beads." npj Clean Water 4.43 (2021): 1-8.

(56) References Cited

OTHER PUBLICATIONS

Li, Huijun, Cavin Tan, and Lin Li. "Review of 3D printable hydrogels and constructs." Materials & Design 159 (2018): 20-38.
Liu, Ying, et al. "Engineering of bio-hybrid materials by electrospinning polymer-microbe fibers." Proceedings of the National Academy of Sciences 106.34 (2009): 14201-14206.
Liu, Bin, et al. "Competition between butyrate fermenters and chain-elongating bacteria limits the efficiency of medium-chain carboxylate production." Frontiers in microbiology 11 (2020): 336.
Liu, Xian-Wei, Guo-Ping Sheng, and Han-Qing Yu. "Physicochemical characteristics of microbial granules." Biotechnology advances 27.6 (2009): 1061-1070.
Lotti, T., et al. "Physiological and kinetic characterization of a suspended cell anammox culture." Water research 60 (2014): 1-14.
Lotti, T., et al. "Pilot-scale evaluation of anammox-based mainstream nitrogen removal from municipal wastewater." Environmental technology 36.9 (2015): 1167-1177.
Lotti, T., et al. "The effect of nitrite inhibition on the anammox process." Water research 46.8 (2012): 2559-2569.
Lu, Yifeng, et al. "Enhancing nitrogen removal performance in a bioreactor using immobilized anaerobic ammonium oxidation sludge by polyvinyl alcohol-sodium alginate (PVA-SA)." Polish Journal of Environmental Studies 27.2 (2018): 773-778.
Magri, Albert, Matias B. Vanotti, and Ariel A. Szögi. "Anammox sludge immobilized in polyvinyl alcohol (PVA) cryogel carriers." Bioresource technology 114 (2012): 231-240.
Dos Santos, Vitor Alexandre Pires Martins. Towards the integration of oxidative and reductive activities: application to nitrogen removal by co-immobilized microorganisms. Wageningen University and Research, 2001.
Matsushige, K., et al. "The effects of temperature on anaerobic filter treatment for low-strength organic wastewater." Environmental Technology 11.10 (1990): 899-910.
Sriram, G., et al. "Oxygen supply without gas-liquid film resistance to Xanthomonas campestris cultivation." Biotechnology and bioengineering 59.6 (1998): 714-723.
Stahl, David A., and José R. de la Torre. "Physiology and diversity of ammonia-oxidizing archaea." Annual review of microbiology 66 (2012): 83-101.
Straka, Levi, et al. "Kinetic implication of moving warm sidestream Anaerobic ammonium oxidizing bacteria to cold mainstream wastewater." Bioresource technology 288 (2019): 121534.
Straka, Levi L., et al. "Affinity informs environmental cooperation between ammonia-oxidizing archaea (AOA) and anaerobic ammoniaoxidizing (Anammox) bacteria." The ISME journal 13.8 (2019): 1997-2004.
Strous, Mare, et al. "The sequencing batch reactor as a powerful tool for the study of slowly growing anaerobic ammonium-oxidizing microorganisms." Applied microbiology and biotechnology 50.5 (1998): 589-596.
Winkler, M-KH, R. Kleerebezem, and M. C. M. Van Loosdrecht. "Integration of anammox into the aerobic granular sludge process for main stream wastewater treatment at ambient temperatures." Water research 46.1 (2012): 136-144.
Bulut, Emine, and Şanli. "Novel ionically crosslinked acrylamidegrafted poly (vinyl alcohol)/sodium alginate/sodium carboxymethyl cellulose pH-sensitive microspheres for delivery of Alzheimer's drug donepezil hydrochloride: Preparation and optimization of release conditions." Artificial Cells, Nanomedicine, and Biotechnology 44.2 (2016): 431-442.
Indonesian Stage 1 Substantive Examination Report received for Indonesian Application No. P00202102530 dated Nov. 30, 2022; 6 pages total (including English Translation).
Wichterle O., Lím D. Hydrophilic Gels for Biological Use. (1960). Nature, 185:117-118.
Wijffels R.H., Hunik J.H., Leenen E.J.T.M., Günther A., de Castro J.M.O., Tramper J, Englund G., Bakketun Å. (1995) Effects of diffusion limitation on immobilized nitrifying microorganisms at low temperatures. Biotechnology and Bioengineering, 45, 1-9.
Ali, M., Oshiki, M., Rathnayake, L., Ishii, S., Satoh, H., Okabe, S. (2015). Rapid and successful start-up of anammox process by immobilizing the minimal quantity of biomass in PVA-SA gel beads. Water research, 79, 147-157.
Costa, L. S. D., Grazziotti, P. H., Silva, A. C., Fonseca, Â. J., Gomes, Å. L. F., Grazziotti, D. C. F. S., Rossi, M. J. (2019). Alginate gel entrapped ectomycorrhizal inoculum promoted growth of cuttings of Eucalyptus clones under nursery conditions. Canadian Journal of Forest Research, 48(8), 978-985.
De Jaeger, N., De la Providencia, I. E., Rouhier, H., Declerck, S. (2011). Co-entrapment of *Trichoderma harzianum* and *Glomus* sp. within alginate beads: impact on the arbuscular mycorrhizal fungi life cycle. Journal of Applied Microbiology, 111(1), 125-135.
Hung, L. L. L., O'Keefe, D. M., Sylvia, D. M. (1991). Use of hydrogel as a sticking agent and carrier for vesicular-arbuscular mycorrhizal fungi. Mycological Research, 95(4), 427-429.
Pitaktamrong, P., Kingkaew, J., Yooyongwech, S., Cha-um, S., Phisalaphong, M. (2018). Development of arbuscular mycorrhizal fungi-organic fertilizer pellets encapsulated with alginate film. Engineering Journal, 22(6), 65-79.
Vassilev, N., Vassileva, M., Azcon, R., Medina, A. (2001). Preparation of gel-entrapped mycorrhizal inoculum in the presence or absence of Yarowia lipolytica. Biotechnology letters, 23(11), 907-909.
Agarwal, T. et al. Calcium alginate-carboxymethyl cellulose beads for colon-targeteddrug delivery, International Journal of Biological Macromolecules 75 (2015) 409-417.
Amidon, S. et al. Colon-Targeted Oral Drug Delivery Systems: Design Trends and Approaches, AAPS PharmSciTech, vol. 16, No. 4, Aug. 2015, 11 pages.
Bashan, Y. et al. Alginate microbeads as inoculant carriers for plant growth-promoting bacteria, Biol Fertil Soils (2002) 35:359-368.
Coussa, R.G. et al. Microencapsulated *Saccharomyces cerevisiae* Column Bioreactor for Potential Use in Renal Failure Uremia, Artificial Cells, Blood Substitutes, and Biotechnology, 40;1-2 (2012) 103-112.
Cowen, A. Boba Spherification: The Science of Juice-filled Caviar, Science Buddies, Oct. 6, 2014, https://www.sciencebuddies.org/blog/boba-spherification-the-science-of-juice-filled-caviar, 4 pages.
Davilas, A. et al. In-vitro study on the competitive binding of diflunisal and uraemic toxins to serum albumin and human plasma using a potentiometric ion-probe technique, Journal of Pharmacy and Pharmacology 2006, 58: 1467-1474.
Dealler, S.F. et al. Enzymatic Degradation of Urinary Indoxyl Sulfate by Providencia stuartii and Klebsiella pneumoniae Causes the Purple Urine Bag Syndrome, Journal of Clinical Microbiology, Oct. 1988, p. 2152-2156.
Evenepoel, P. et al. Uremic toxins originating from colonic microbial metabolism, Kidney International (2009) 76 (Suppl 114), S12-S19.
Fang, C.Y. et al. Selection of uremic toxin-reducing probiotics in vitro and in vivo, Journal of Functional Foods 7 (2014) 407-415.
Gosmann, B. et al. Oxygen uptake of microorganisms entrapped in Ca-alginate, Applied Microbiology and Biotechnology vol. 23, pp. 163-167(1986).
Gramigna, J. Probiotics may reduce urea in patients with nondialysis CKD, Healio, Dec. 31, 2018, https://www.healio.com/news/nephrology/20181231/probiotics-may-reduce-urea-in-patients-with-nondialysis-ckd, 2 pages.
Hida, M. et al. Inhibition of the Accumulation of Uremic Toxins in the Blood and Their Precursors in the Feces after Oral Administration of Lebenin®, a Lactic Acid Bacteria Preparation, to Uremic Patients Undergoing Hemodialysis, Nephron, 1996;74 (2) 349-355.
Jain, P. Potentials and limitations of microorganisms as renal failure biotherapeutics, Biologics: Targets & Therapy 2009:3 233-243.
Johansen, A. et al. Immobilization of yeast cells by internal gelation of alginate, Enzyme and Microbial Technology, vol. 8 No. 3, Mar. 1986, 145-148.
Koppe, L. Probiotics and chronic kidney disease, Kidney International (2015) 88, 958-966.
Krasaekoopt, W. et al. The influence of coating materials on some properties of alginate beads and survivability of microencapsulated probiotic bacteria, International Dairy Journal 14 (2004) 737-743.

(56) References Cited

OTHER PUBLICATIONS

Lekawanvijit, S. et al. The Uremic Toxin Adsorbent AST-120 Abrogates Cardiorenal Injury Following Myocardial Infarction, PLoS One. 2013; 8(12): e83687.
Lin, J. et al. In Vitro and in Vivo Characterization of Alginate-Chitosan-Alginate Artificial Microcapsules for Therapeutic Oral Delivery of Live Bacterial Cells, Journal of Bioscience and Bioengineering, 105(6); Jun. 2008, 660-665.
Miranda Alatriste, P.V. et al. Effect of probiotics on human blood urea levels in patients with chronic renal failure, Nutr Hosp. 2014;29(3):582-590.
O'Loughlin, J.A. et al. Degradation of low molecular weight uremic solutes by oral delivery of encapsulated enzymes, ASAIO J. May-Jun. 2004;50(3):253-60.
O'Loughlin, J.A. et al. In Vivo and in Vitro Degradation of Urea and Uric Acid by Encapsulated Genetically Modified Microorganisms, Tissue Engineering, vol. 10, No. 9/10, 2004.
Prakash, S. et al. Microencapsulated genetically engineered live *E.coli* DHS cells administered orally to maintain normal plasma urea level in uremic rats, Nature Medicine, vol. 2, No. 8, Aug. 1996, 883-887.
Takayama, F. et al. Bifidobacterium in Gastro-Resistant Seamless Capsule Reduces Serum Levels of Indoxyl Sulfate in Patients on Hemodialysis, American Journal of Kidney Diseases, vol. 41, No. 1, Suppl 1 (March), 2003: pp S142-S145.
Tao, S. et al. Effects of probiotic supplements on the progression of chronic kidney disease: A meta-analysis, Nephrology 24 (2019) 1122-1130.
Wang, J.Y. et al. Application of hydrogel encapsulated carbonate precipitating bacteriafor approaching a realistic self-healing in concrete, Construction and Building Materials 68 (2014) 110-119.
Zheng, D.W. et al. An orally delivered microbial cocktail for the removal of nitrogenous metabolic waste in animal models of kidney failure, Nature Biomedical Engineering vol. 4, pp. 853-862(2020).
International Search Report mailed Jan. 2, 2020, issued in corresponding International Application No. PCT/US2019/056119, filed on Oct. 14, 2019, 2 pages.
Geiser, L., Patel-Weynand, T., Marsh, A., Mafune K., Vogt, D. Chapter 10: Challenges and Opportunities. In: Sustainable Forest Management Research—Forest and rangeland soils of the United States under changing conditions: A comprehensive science synthesis. National Soils Assessment. Anticipated release 2020.
Mafune, K., Godfrey, B., Vogt, K., and Vogt, D (2019). A rapid approach to profiling diverse fungal communities using the MinION™ nanopore sequencer. Biotechniques, 68(2), 72-78.
Schmer M.R., Vogel K.P., Mitchell R.B., Perrin R.K. (2018) Net energy of cellulosic ethanol from switchgrass. Proceedings of the National Academy of Sciences. 105:464-469.
Service, R. (2018). Ammonia—A Renewable Fuel Made From Sun, Air, and Water—Could Power the Globe Without Carbon. Science, aau7489.
Smith, K.A. (2017). Changing views of nitrous oxide emissions from agricultural soil: key controlling processes and assessment at different spatial scales. European Journal of Soil Science, 68(2), 137-155.
Fagodiya, R. K., Pathak, H., Kumar, A., Bhatia, A., Jain, N. (2017). Global temperature change potential of nitrogen use in agriculture: A 50-year assessment. Scientific reports, 7(44928).
Fageria, N. K., & Baligar, V. C. (2005). Enhancing nitrogen use efficiency in crop plants. Advances in agronomy, 88, 97-185.
Dodds, W. K. et al. (2009) Eutrophication of U.S. freshwaters: analysis of potential economic damages. Environmental Science and Technology, 43(12-19).
Sinha, E., Michalak, A. M., Balaji, V. (2017). Eutrophication will increase during the 21st century as a result of precipitation changes. Science, 357(6349), 405-408.
Liu, J., Ma, K., Ciais, P., Polasky, S. (2016). Reducing human nitrogen use for food production. Scientific reports, 6, 30104.
Pannu MW, Meinhardt KA, Bertagnolli A, Fransen SC, Stahl DA, Strand SE (2019). Nitrous oxide emissions associated with ammonia-oxidizing bacteria abundance in fields of switchgrass with and without intercropped alfalfa. Environmental Microbiology Reports, 11(727-735).
Frankow-Lindberg, B.E., A.S. Dahlin. (2013). N2 fixation, N transfer, and yield in grassland communities including a deep-rooted legume or non-legume species. Plant and Soil, 370, 567-581.
Burton, J.C. (1972). Nodulation and symbiotic nitrogen fixation. In C.H. Hanson (Ed.), Alfalfa Science and Technology (Monograph 15; pp. 229-246). Madison, WI: American Society of Agronomy.
Reed S.C., Cleveland C.C., Townsend A.R. (2011). Functional ecology of free-living nitrogen fixation: a contemporary perpective. Annu Rev Ecol Evol Syst 42: 489-512.
Norman, J. S., Friesen, M. L. (2017). Complex N acquisition by soil diazotrophs: how the ability to release exoenzymes affects N fixation by terrestrial free-living diazotrophs. The ISME journal, 11(2), 315-326.
Islam, M. R., Sultana, T., Joe, M. M., Yim, W., Cho, J. C., Sa, T. (2013). Nitrogen—fixing bacteria with multiple plant growth-promoting activities enhance growth of tomato and red pepper. Journal of basic microbiology, 53(12), 1004-1015.
Jeffries, P., & Barea, J. M. (2001). Arbuscular mycorrhiza—a key component of sustainable plant-soil ecosystems. In Fungal Associations (pp. 95-113). Springer, Berlin, Heidelberg.
Farzaneh, M.,Vierheilig, H., Lössl, A., Kaul, H. P. (2011). Arbuscular mycorrhiza enhances nutrient uptake in chickpea. Plant, Soil and Environment, 57(10), 465-470.
Mosse, B. (1977). Plant growth responses to vesicular-arbuscular mycorrhiza: Responses of Stylosanthes and Maize to inoculation in unsterile soils. New phytologist, 78(2), 277-288.
Ahanger, M. A., Hashem, A., Abd-Allah, E. F., Ahmad, P. (2014). Arbuscular mycorrhiza in crop improvement under environmental stress. In Emerging technologies and management of crop stress tolerance (pp. 69-95). Academic Press.
Miransari, M., Bahrami, H. A., Rejali, F., Malakouti, M. J. (2008). Using arbuscular mycorrhiza to alleviate the stress of soil compaction on wheat (*Triticum aestivum* L.) growth. Soil Biology and Biochemistry, 40(5), 1197-1206.
Barea, J. M., Azcón, R., Azcón-Aguilar, C. (2002). Mycorrhizosphere interactions to improve plant fitness and soil quality. Antonie van leeuwenhoek, 81(1-4), 343-351.
Ghignone, S., Salvioli, A., Anca, I., Lumini, E., Ortu, G., Petiti, L., Bonfante, P. (2012). The genome of the obligate endobacterium of an AM fungus reveals an interphylum network of nutritional interactions. The ISME journal, 6(1), 136-145.
Paul, K., Saha, C., Nag, M., Mandal, D., Naiya, H., Sen, D., Naskar, N. (2020). A tripartite interaction among the basidiomycete Rhodotorula mucilaginosa, N2-fixing endobacteria, and rice improves plant nitrogen nutrition. The Plant Cell, 32(2), 486-507.
Gómez-Brandón, M., Probst, M., Siles, J. A., Peintner, U., Bardelli, T., Egli, M., Ascher-Jenull, J. (2020). fungal communities and their association with nitrogen—fixing bacteria affect early decomposition of Norway spruce deadwood. Scientific reports, 10(1), 1-11.
USDA State Overview for Washington. Website: https://www.nass.usda.gov/Quick_Stats/Ag_Overview/stateOverview.php?state=WASHIGTON.
Ballesteros, I., Negro, M. J., Oliva, J. M., Cabañas, A., Manzanares, P., Ballesteros, M. (2006). Ethanol production from steam-explosion pretreated wheat straw. In Twenty seventh symposium on biotechnology for fuels and chemicals (pp. 496-508). Humana Press.
Barros-Rios, J., Romaní, A., Garrote, G., Ordas, B. (2015). Biomass, sugar, and bioethanol potential of sweet corn. Gcb Bioenergy, 7(1), 153-160.
Persson, T., Ren, J. L., Joelsson, E., Jönsson, A. S. (2009). Fractionation of wheat and barley straw to access high-molecular-mass hemicelluloses prior to ethanol production. Bioresource Technology, 100(17), 3906-3913.
Castellano-Hinojosa, A., Correa-Galeote, D., González-López, J., Bedmar, E. J. (2020). Effect of nitrogen fertilisers on nitrous oxide emission, nitrifier and denitrifier abundance and bacterial diversity in closed ecological systems. Applied Soil Ecology, 145, 103380.
Delgado, J. A., Khosla, R., Bausch, W. C., Westfall, D. G., Inman, D. J. (2005). Nitrogen fertilizer management based on site-specific

(56) References Cited

OTHER PUBLICATIONS management zones reduces potential for nitrate leaching. Journal of Soil and Water Conservation, 60 (6), 402-410.
Schimel, J. (2013). Soil carbon: microbes and global carbon. Nature Climate Change, 3(10), 867.
Wilpiszeski, R. L., Aufrecht, J. A., Retterer, S. T., Sullivan, M. B., Graham, D. E., Pierce, E. M., Elias, D. A. (2019). Soil aggregate microbial communities: Towards understanding microbiome interactions at biologically relevant scales. Applied and environmental microbiology, 85(14), e00324-19.
Bolger, A. M., Lohse, M., Usadel, B. (2014). Trimmomatic: a flexible trimmer for Illumina sequence data. Bioinformatics, 30(15), 2114-2120.
Meyer, F., Paarmann, D., D'Souza, M., Olson, R., Glass, E. M., Kubal, M., Wilkening, J. (2008). The metagenomics RAST server—a public resource for the automatic phylogenetic and functional analysis of metagenomes. BMC bioinformatics, 9(1), 386.
Tang, K., Liu, K., Jiao, N., Zhang, Y., Chen, C. T. A. (2013). Functional metagenomic investigations of microbial communities in a shallow-sea hydrothermal system. PloSone, 8(8), e72958.
Romero-Olivares, A. L., Meléndrez-Carballo, G., Lago-Lestón, A., Treseder, K. K. (2019). Soil metatranscriptomes under long-term experimental warming and drying: fungi allocate resources to cell metabolic maintenance rather than decay. Frontiers in microbiology, 10(1), 1914.
R Core Team (2014). R: A language and environment for statistical computing. R Foundation for Statistical Computing, Vienna, Austria. URL http://www.R-project.org/.
Katoh, K. and Standley, D. M. (2013). MAFFT multiple sequence alignment software version 7: improvements in performance and usability. Molecular biology and evolution, 30(4), 772-780.
Stamatakis, A. (2014). RAxML version 8: a tool for phylogenetic analysis and postanalysis of large phylogenies. Bioinformatics, 30(9), 1312-1313.
Langmead, B. and Salzberg, S. L. (2013). Fast gapped-read alignment with bowtie2. Nature Methods 9(1), 357-359.
Broberg, M., Doonan, J., Mundt, F., Denman, S., and McDonald, J. E. (2018). Integrated multi-omic analysis of host-microbiota interactions in acute oak decline. Microbiome, 6(1), 21.
Haas, B. J., Papanicolaou, A., Yassour, M., Grabherr, M., Blood, P. D., Bowden, J., MacManes, M. D. (2013). De novo transcript sequence reconstruction from RNA-seq using the Trinity platform for reference generation and analysis. Nature protocols, 8(8), 1494.
Bryant, D. M., Johnson, K., DiTommaso, T., Tickle, T., Couger, M. B., Payzin-Dogru, D., Whited, J.L. (2017). A tissue-mapped axolotl de novo transcriptome enables identification of limb regeneration factors. Cell Reports., 18(1), 762-776.
Cai, Y., Zheng, Y., Bodelier, P. L., Conrad, R., Jia, Z. (2016). Conventional methanotrophs are responsible for atmospheric methane oxidation in paddy soils. Nature communications, 7(1), 11728.
Yergeau, E., Sanschagrin, S., Maynard, C., St-Arnaud, M., Greer, C. W. (2014). Microbial expression profiles in the rhizosphere of willows depend on soil contamination. The ISME journal, 8(2), 344.
Deppe, M., Knorr, K. H., McKnight, D. M., Blodau, C. (2010). Effects of short-term drying and irrigation on $CO_2$ and $CH_4$ production and emission from mesocosms of a northern bog and an alpine fen. Biogeochemistry, 100(1-3), 89-103.
Peng, B., Sun, J., Liu, J., Dai, W., Sun, L., Pei, G., Bai, E. (2019). N2O emission from a temperate forest soil during the freeze-thaw period: A mesocosm study. Science of the Total Environment, 648, 350-357.
Dobermann, Achim R., "Nitrogen Use Efficiency—State of the Art" (2005). Agronomy & Horticulture—Faculty Publications. 316. https://digitalcommons.unl.edu/agronomyfacpub/316.
Bahram, M., Mohseni, N., Moghtader, M. (2016). An introduction to hydrogels and some recent applications. In Emerging concepts in analysis and applications of hydrogels. IntechOpen.
Office Action mailed Aug. 9, 2023, issued in corresponding IL Application No. 282091, filed Oct. 14, 2019, 6 pages.
International Search Report and Written Opinion mailed Jun. 14, 2023, issued in corresponding International Application No. PCT/US2023/060180, filed Jan. 5, 2023, 10 pages.
Martinez-Cano, B., et al., "Review and Perspectives of the Use of Alginate as a Polymer Matrix for Microorganisms Applied in Agro-Industry," Molecules 2022, 27, 4248, 20 pages.
Suman, A., et al., "Development of Hydrogel based Bio-Inoculant Formulations and their Impact on Plant Biometric Parameters of Wheat (*Triticum aestivum* L.)," Int. Journal Curr. Microbiol. App. Sci (2016) 5(3): 890-901.
Search Report mailed Jun. 6, 2023, issued in corresponding Taiwanese Application No. 108136937, filed Oct. 14, 2019, 7 pages.
Tomaro-Duchesneau, C., et al., "Microencapsulation for the therapeutic delivery of drugs, live mammalian and bacterial cells, and other biopharmaceutics: current status and future directions," Journal of Pharmaceutics 2013, Article ID 103527, 27 pages.
Notice of Reasons for Refusal mailed Aug. 4, 2023, issued in corresponding Japanese Application No. 2021-519807, filed Oct. 14, 2019, 13 pages.
Examiner's Decision of Refusal (with translation) for No. 2021-519807, filed Oct. 14, 2019; 15 pages total.
English translation of patent publication JP-10180282A, published Jul. 7, 1998. (Year: 1998).
English translation of Patent Publication JP3361570 published Jan. 7, 2003. (Year: 2003).
English translation of patent publication JP-2004033808A, published Feb. 5, 2004. (Year: 2004).
English translation of Patent Publication CN107324616, published Nov. 7, 2017. (Year: 2017).
English translation of Patent Publication CN109734174, published May 10, 2019. (Year: 2019).
Office Action (Non-Final Rejection) dated Aug. 19, 2024 for U.S. Appl. No. 17/767,613 (pp. 1-21).

\* cited by examiner

SYSTEM AND METHOD FOR REMOVING UREMIC TOXINS FROM A PATIENT'S BODY

CROSS-REFERENCE TO RELATED APPLICATION

This application claims the benefit of U.S. Patent Application No. 62/744,966, filed Oct. 12, 2018, which is expressly incorporated herein by reference in its entirety.

BACKGROUND

Kidney disease afflicts ten percent of the world population and presents a major health burden. Dialysis and renal transplants are the only treatment options at the present time. However, the economic costs of these treatment methods are extremely high.

Several treatment attempts have been based on the use of the digestive system as a substitute for kidney function. During a normal digestive process, the gastrointestinal tract delivers nutrients and water to the bloodstream and eliminates waste products and undigested materials through the bowel. The intestinal wall regulates absorption of nutrients, electrolytes, water, and certain digestive aiding substances, such as bile acids. The intestinal wall also acts as a semipermeable membrane allowing small molecules to pass from the intestinal tract into the bloodstream and preventing larger molecules from entering the circulation. Various invasive and noninvasive attempts, including external gut fistula, intestinal dialysis, induced diarrhea, and administration of oral sorbents and/or encapsulated urease enzyme have been made to extract uremic waste from the gastrointestinal tract.

Oxystarch, locust bean gum, and other substances have been studied as potential oral sorbents for treatment of uremia. Encapsulated urease enzymes have also been investigated as nonabsorbable oral sorbents for binding ammonia. Some genetically engineered microorganisms have been encapsulated and shown to be effective in removal of urea and ammonia in an in vitro system and in uremic rat animal models. However, none of these treatments have been able to remove uremic toxins in amounts sufficient to reduce uremia symptoms in patients with kidney failure. Moreover, none of these systems has been able to address accumulation of indoxyl sulfate, a major uremic toxin, in the blood.

There is a need for more effective treatments that can remove multiple uremic toxins effectively from the digestive tract before they enter the bloodstream to alleviate the symptoms of uremia in patients.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a composition for reducing concentration of one or more uremic toxins or uremic toxin precursors in a patient's digestive system is provided. In one embodiment, the composition includes a plurality of hydrogel particles, each particle comprising an agent encapsulated within the particle and configured to reduce a local concentration of one or more uremic toxins or uremic toxin precursors.

In another aspect, a method for reducing concentration of one or more uremic toxins in a patient's digestive system is provided. In one embodiment, the method includes administering a composition as disclosed herein to a patient in need thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5C and 5C are images of the ~3 mm diameter beads produced. A small "stem" that was sometimes found on the gel beads because of the non-spherical shape of the alginate droplets that initially contacted the $CaCl_2$ solution using this particular method to form the beads (5C).

Figure 1A:
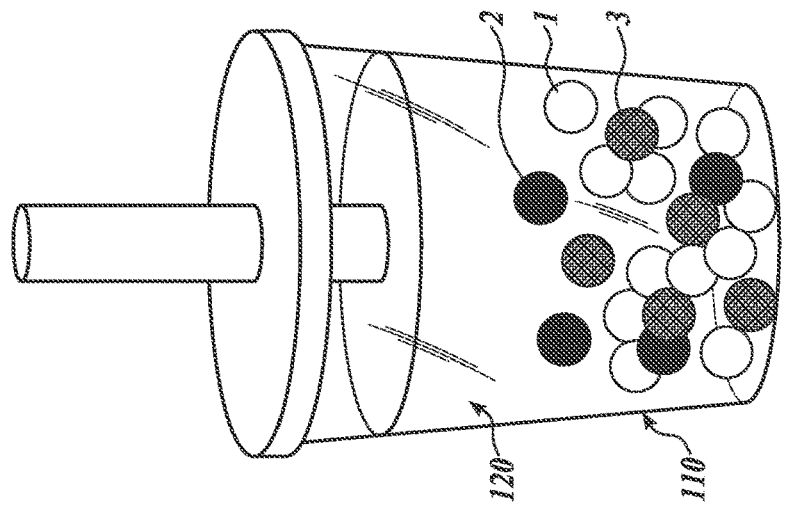
FIGS. 1A-C depicts exemplary compositions in the form of a therapeutic drink A composition can comprise one or more types of particles suspended in a drinkable fluid, such that the particles can be ingested through a straw. Each type of particle can be configured to remove one or more uremic toxins or precursors to uremic toxin by one of several means, including absorption by inorganic or organic molecules, including proteins and peptides, or live colonies of organisms, including bacteria, yeasts or fungi.

*E. coli* removed more glucose from the surrounding buffer than beads containing heat-killed *E. coli*. Thin bars represent standard deviation (n=2).

DETAILED DESCRIPTION

The present disclosure is related to compositions and methods for reducing the concentration of uremic toxins in the body of a patient suffering from some degree of kidney failure. In some cases, the compositions and methods can be used to delay the need for conventional dialysis treatment or can be used as an adjunct therapy to reduce the frequency of dialysis sessions, and in some instances, as an alternative to such dialysis sessions.

Thus, in one aspect, disclosed herein is a composition for reducing concentration of one or more uremic toxins or uremic toxin precursors in a patient's digestive system, comprising a plurality of hydrogel particles, each particle comprising an agent encapsulated within the particle and configured to reduce a local concentration of one or more uremic toxins or uremic toxin precursors. In some embodiments, each particle can comprise two agents. In some embodiments, each particle can comprise three agents, four agents, or five agents, such as bacteria strains.

Uremic toxins are compounds that are usually filtered and excreted by the kidneys, such as urea and indoxyl sulfate, but are accumulated in the blood of chronic kidney disease (CKD) patients. As used herein, a uremic toxin precursor is a compound that can be converted into a uremic toxin in the body. For example, indoxyl sulfate, a uremic toxin, is produced by the liver. A part of the dietary protein-derived amino acid tryptophan is metabolized by intestinal bacteria into indole, which is subsequently metabolized to indoxyl sulfate in the liver. Thus, in some embodiments, removal of one or more uremic toxin precursors generated in the digestive system, such as indole, is desirable for managing CKD. Alternatively, it is possible to reduce the concentration of the precursor to indole (tryptophan) in the gut to the same effect.

Any suitable agent capable of reducing the concentration of one or more uremic toxins or uremic toxin precursors can be included in the compositions disclosed herein. In some embodiments, the agent is configured to reduce a local concentration of one or more uremic toxins or uremic toxin precursors in a patient's digestive tract, including the colon.

In some embodiments, the agent is a colony of microorganisms. Examples of suitable microorganisms include but are not limited to bacteria, yeasts, molds, and both natural and genetically-engineered organisms. In some embodiments, the agent can include a probiotic composition. In some embodiments, the prebiotic composition can comprise *Propionibacterium*, a *Lactobacillus*, a *Bifidobacterium*, a *Streptococcus*, or a combination thereof. Suitable bacteria that can be used in the compositions of the disclosure also include bacteria, such as *E. coli*, that have been gene-engineered, for instance, to express one or more enzymes that convert a uremic toxin or a uremic toxin precursor into a non-toxic compound or otherwise render a uremic toxin or a uremic toxin precursor non-toxic.

In some embodiments, the colony of microorganisms comprises one or more microbial strains configured to utilize the one or more uremic toxins or uremic toxin precursors as a food source. In some embodiments, the colony of microorganisms comprises one or more microbial strains configured to convert the one or more uremic toxins or uremic toxin precursors into one or more non-toxic substances. In some embodiments, the colony of microorganisms comprises one or more microbial strains configured to convert the one or more uremic toxins or uremic toxin precursors into one or more non-toxic substances that precipitates inside the hydrogel particles. In some embodiments, the microorganisms are configured to convert the one or more uremic toxins to biomass by increasing the number of microorganisms in the hydrogel particle. Microorganisms included in the compositions disclosed herein include live and inactivated microbial cultures.

In some embodiments, the microorganisms can be contained within the hydrogel so that the microorganisms do not escape from the hydrogel and/or do not alter the patient's gut microbiome.

In some embodiments, each particle of the composition comprises at least two of microorganisms. In some embodiments, each particle of the composition comprises at least two co-resident types of microorganisms.

In some embodiments, the agent is a sorbent agent, such as an adsorbent agent or an absorbent agent, configured to non-covalently bind one or more uremic toxins or uremic toxin precursors, and that can be immobilized within the gel bead to prevent escape into the gut. Suitable sorbent agents include both organic and inorganic sorbents. In some embodiments, the sorbent agent is a protein or a de novo designed peptide or an antibody that can bind one or more one or more uremic toxins or uremic toxin precursors, either specifically or non-specifically. In some embodiments, the sorbent agent is albumin. In some embodiments, the sorbent agent is bovine serum albumin (BSA). In some embodiments, the agent binds tryptophan or indole.

In some embodiments, the agents include inorganic adsorbents, such as charcoal.

In some embodiments, the hydrogel particles comprise spherical hydrogel particles. In some embodiments, the spherical hydrogel particles have a diameter from about 0.1 mm to about 10 mm, from about 1 mm to about 10 mm, from about 2 mm to about 8 mm, or from about 3 mm to about 5 mm. As used herein, the term "about" means ±5% of the stated value. The size of the sphere can determine not only the load of the agent, e.g., bacterial organisms, but also the rate at which the toxins reach the agent.

In some embodiments, the hydrogels particles are substantially spherical or sphere-like, with both terms indicating the hydrogel particles are not perfect spheres but have substantially spherical character. Substantially spherical particles include particles with ellipsoidal dimensions, "teardrop" shaped particles, and particles with surface features such as pock marks or indentations.

In some embodiments, the hydrogels particles are not spherical. Other than spherical hydrogel geometries can be configured, and different sizes and shapes can be mixed and matched. For example, in some embodiments, cube-like shapes and a cylinder-like shapes can be used.

Any type of biocompatible hydrogel can be used in the compositions disclosed herein. In some embodiments, the hydrogel or a portion thereof is indigestible. As used herein, "indigestible" refers to a material that can pass through a GI tract, e.g., of a human, substantially intact. Examples of indigestible hydrogels include but are not limited to agar, alginate, and other natural carbohydrate-based gel-formers. Other examples of the hydrogels suitable for inclusion in the compositions disclosed herein are synthetic polymers that form hydrogels such as polyacrylamide, silicones, and polyethylene glycol (PEG or PEO) polymers.

The hydrogels included in the compositions comprise non-toxic components. In some embodiments, the hydrogel comprises components that have been designated as "generally regarded as safe" (GRAS). In some embodiments, the hydrogels comprise components such as polymers approved by the FDA for human or animal consumption. In some embodiments, the hydrogels included in the compositions are non-toxic.

Typically, the hydrogels are porous and allow diffusion of uremic toxins or their precursors to the agents, such as microorganisms, encapsulated within the particles of the compositions.

In some embodiments, the hydrogel is a hydrogel that supports growth of the microorganisms, allows in-diffusion of the uremic toxins or their precursors, and optionally required nutrients and gases, to the microorganisms, but prevents the toxin-removing microorganisms from being released into the gut microbiome, and is not itself toxic to the patient.

Hydrogel particles suitable for inclusion in the compositions of the disclosure can be produced by methods known in the art. For example, alginate hydrogels can be produced by crosslinking sodium alginate in the presence of divalent cations, such as calcium or barium cations. In some embodiments, the hydrogels are covalently crosslinked. In some embodiments, the hydrogels are calcium alginate (CA)-carboxymethyl cellulose (CMC) hydrogels. In some embodiments, the hydrogels are prepared by entrapping an agent, such as BSA, in calcium alginate hydrogel and then further crosslinking the agent entrapped in the hydrogel, for example, crosslinking the amino groups of BSA entrapped in alginate hydrogels with glutaraldehyde. In some embodiments, the crosslinked entrapped agents, e.g., albumin, molecules can form a second hydrogel within the hydrogel of the particle, such as alginate hydrogel, which is itself only crosslinked by the electrostatic bonds to the $Ca^{++}$ ions. Methods of crosslinking of hydrogels comprising reactive groups, such as amino, carboxy, and hydroxy groups, are known in the art. In some embodiments, the hydrogel particles comprise an interpenetrating network comprising a hydrogel, such as alginate, and a crosslinked protein, such as albumin (e.g., BSA).

Several types of gel-forming materials can be used to make the hydrogel particles of the disclosed compositions and to encapsulate the agents, e.g., immobilize bacteria, within hydrogel particles. In some embodiments, the hydrogels are made from inexpensive commodity materials which are non-toxic, primarily alginate (sodium alginate or SA) and poly(vinyl alcohol) (PVA), and/or acrylate derivatives of polyethylene glycol such as PEG diacrylate (PEGDA) and PEG dimethacrylate (PEGDMA).

In some embodiments, thiol and norbornene derivatives of PEG can be used and optionally conveniently crosslinked using photo-activatable cross-linking chemistry. In some embodiments, the agent, such as bacteria, is immobilized by mixing a bacterial cell suspension with a sodium alginate solution and dripping this mixture into a calcium chloride bath, where the calcium ions form ionic crosslinks between the alginic acid chains and cause the solution droplets to gel into particles, e.g., beads. The same ionic cross-linking method can be used to prepare particles from mixtures of alginate and PVA, (PVA/SA). In some embodiments, PVA can be crosslinked by including a photo-crosslinkable styrylpyridinium PVA derivative, SbQ-PVA, in the mixture.

In some embodiments, the hydrogels comprise PEG hydrogels, e.g., hydrogels prepared from PEG acrylates. In some embodiments, PEG hydrogels can be resistant to biodegradation in the gastrointestinal tract. In some embodiments, bacterial immobilization in PEG hydrogels can be done using a sheet casting approach where the hydrogels with immobilized bacteria are formed as sheets which are subsequently cut into small cubes.

In some embodiments, a hybrid approach can be used to prepare the hydrogel particles of the compositions disclosed herein. The hybrid approach uses ionic alginate dripping method, using a $Ca^{+2}$ bath to initially form the bead structure of a SA/PEG acrylate polymer mix, while simultaneously starting the free radical initiation process to cross-link the PEG acrylate prepolymer component before it diffuses out of the alginate gel.

Particles of varying sizes can be formed using methods known in the art, for example in a T-channel fluidic or microfluidic device by varying the flow rates of the oil and aqueous phases. This method allows precise control of particle sizes, at the cost of very low throughput and the necessity for an oil-removing step. In some embodiments, for instance, when particles are formed from PVA/SA mixtures as described above, the polymer solutions can be quite viscous; this process results in about 3 mm diameter particles produced by dripping the polymer solution through a fine needle orifice. Smaller breads, down to about 0.5 mm, can be made if a strong electrostatic field is applied between the needle and the receiving solution, e.g. calcium chloride solution.

Figure 2A:
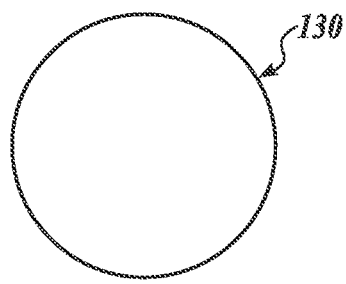
FIGS. 2A-C show architecture of exemplary particles suitable for inclusion in the compositions disclosed herein.
Figure 2B:
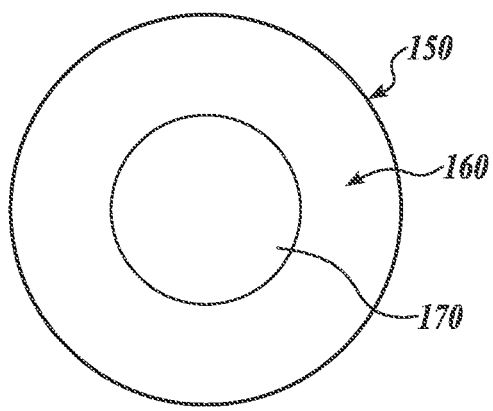
Figure 2C:
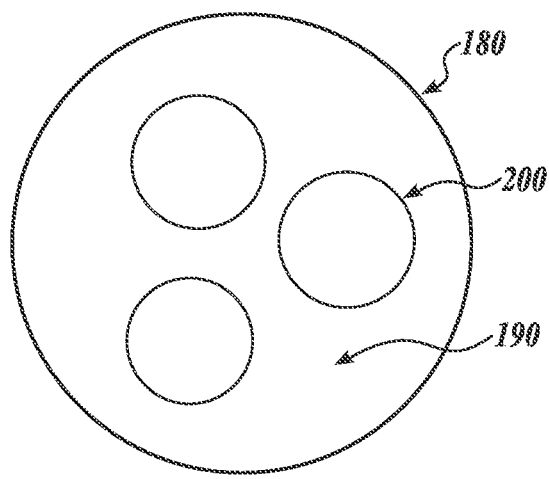

The hydrogel particles disclosed herein can have various architecture, non-limiting examples of which are shown in FIGS. 2A-C. In some embodiments, the hydrogel particles (130) can be in the form of solid particles comprising a single type of hydrogel (FIG. 2A). In some embodiments, the hydrogel particles disclosed herein (150) can comprise a core (170) and one or more outer shell layers (160) surrounding the core, as shown in FIG. 2B. In some embodiments, the hydrogel particles disclosed herein (180) can have several smaller particles (200) embedded in a larger hydrogel particle (180) comprising a different type of hydrogel (190), as shown in FIG. 2C.

In some embodiments, the agent, e.g., bacteria or sorbent, is in the core of the particle. In some embodiments, the agent, e.g., bacteria or sorbent, is both in the core and in the shell of the particle. In some embodiments, the shell of the particle allows diffusion of uremic toxins into the core. In some embodiments, the core comprising the agent, e.g., bacteria or sorbent, comprises indigestible hydrogel. In some embodiments, the shell comprises a polymer or another material that acts as an enteric coating and/or protects the particle core and the agent immobilized within the core from the acidic environment of the stomach.

In some embodiments, the compositions disclosed herein further comprise a fluid carrier. Any suitable fluid carrier that facilitates the ingestion of the gel particles and is not toxic to the patient can be used in the compositions disclosed herein. For example, in some embodiments, the fluid carrier can comprise broth, soup, tea, coffee, milk, fruit puree, juice, or combinations thereof. In some embodiments, one or more sweeteners, food colorants, nutrients, flavoring agents, or combinations thereof can be included in the compositions disclosed herein.

Figure 1B:
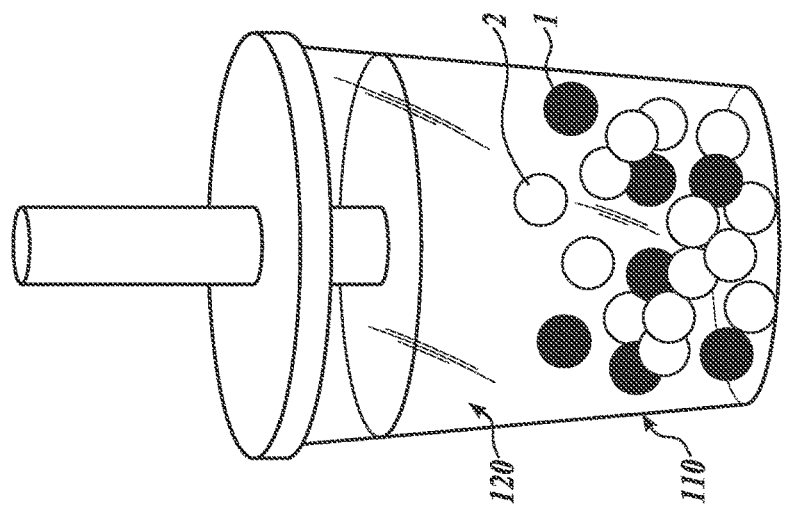
Figure 1C:
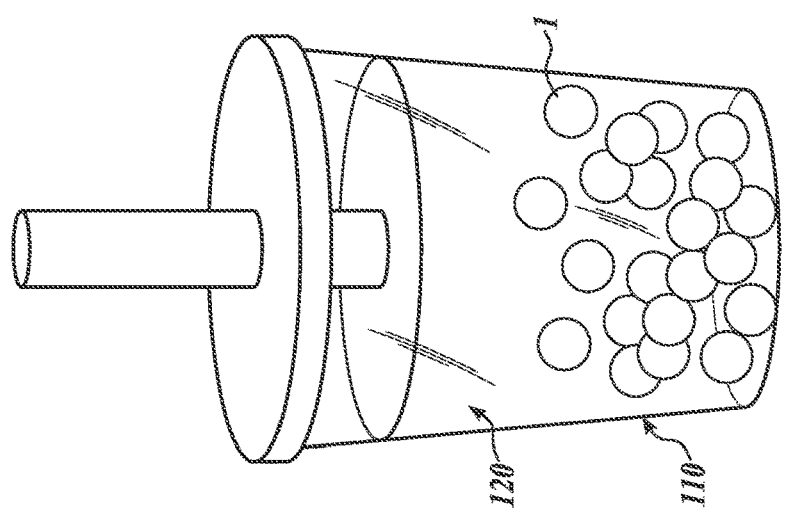

In some embodiments, the compositions disclosed herein can be used as a therapy for kidney failure. In some embodiments, a composition of the disclosure comprising one or more types of hydrogel particles and a fluid carrier can be provided to a patient suffering from a kidney failure as therapeutic beverage, similar to a popular drink known as "bubble tea" which can be consumed, for example, through a straw from a beverage container. FIGS. 1A-C depict some embodiments of such therapeutic drinks in containers (110), wherein the drink comprises a fluid carrier (120) and one or more types of hydrogel particles (1, 2, 3). In some embodiments, the therapeutic drink, i.e., a composition of the disclosure, comprises a fluid carrier (120) and one type of particles (1) as shown in FIG. 1A. In some embodiments, the therapeutic drink, i.e., a composition of the disclosure, comprises a fluid carrier (120) and more than one type of particles, such as two type of particles (1 and 2) as shown in FIG. 1B. In some embodiments, the therapeutic drink, i.e., a composition of the disclosure, comprises a fluid carrier (120) and more than two type of particles, such as three type of particles (1, 2, and 3) as shown in FIG. 1C. Each type of hydrogel particle can be configured to reduce the concentration of a particular uremic toxin or a precursor thereof.

When the particles reach a portion of the GI tract where the agents or their precursors begin to accumulate, e. g, a patient's colon, the agents, e.g., microorganisms, within each particle can absorb and/or bioconvert the one or more uremic toxins. The hydrogel particles are then excreted intact in feces along with the encapsulated agents, e.g., microorganisms, along with any excess fluids that may have also been absorbed, thus not contaminating the gut flora with the agent encapsulated in the particle. The composition of the therapeutic drink and/or dose of any particular particle can be tailored to the needs of individual patient, e.g., by adjusting the number and ratios of the toxin-specific hydrogel particles in each drink.

In some embodiments, the compositions disclosed herein are consumed as part of a neutral or nutritious drink. In some embodiments, wherein the patients have developed their kidney dysfunction as a result of type 2 diabetes, the compositions can be sugar-free. In some embodiments, the disclosed herein compositions can be offered in flavored, sweet, or savory forms (for example, a chicken-broth-based "bubble tea"). In some embodiments, the fluid carrier included in the composition disclosed herein can be tailored to the individual nutritional needs of the patients, based on their diets and degree of kidney dysfunction. The therapeutic drink, i.e., a composition disclosed herein, can also provide a very positive and enjoyable experience for a patient. Thus, in some embodiments, the types of hydrogel particles can be color-coded by including a food compatible dye in the composition, thereby resulting in a colorful drink. Mixing and matching the "spheres," i.e., hydrogel particles, with appropriate agents, e.g., bacterial strains, in a patient-specific ratio can also be used to tailor the therapy to the particular diet consumed by the patient. For example, a ratio of tryptophan-removing particles can be increased in the composition to be consumed prior to a large protein-rich meal.

In some embodiments, the hydrogel particles can be stored in dry form prior to addition of a carrier and/or administration in the form of a therapeutic drink. In some embodiments, the agents, such as microorganisms, included in the hydrogel particles of the compositions of the disclosure can be dried and reactivated upon rehydration.

Thus, in another aspect, provided herein is a method for reducing a concentration of one or more uremic toxins in a patient's digestive system, comprising administering the composition of the disclosure to a patient in need thereof. In some embodiments, the patient is a human patient, such as a patient diagnosed with a kidney failure. In some embodiments, the patient is a veterinary patient, e.g., a canine or feline (domestic dog or cat). For veterinary applications, the compositions of the disclosure, in addition to the hydrogel particles, can further comprise a matrix, such as a pureed chicken or beef, suitable for administration to a veterinary patient, for example, via syringe feeding. For veterinary application, the size of the hydrogel particles can be selected such that would allow the particles to be swallowed by the patient without chewing, to travel through the GI tract without blocking it, and to be excreted.

In some embodiments, the methods of treatment of the present disclosure can be used to delay the need for conventional dialysis treatment. In some embodiments, the methods of treatment of the present disclosure can be used as an adjunct therapy, for example, to reduce the frequency of dialysis sessions or as a replacement for some of the dialysis sessions. As used herein, "adjunctive therapy" is a therapy that allows to reduce the concentration of one or more uremic toxins or precursors thereof that are poorly removed from the bloodstream even by dialysis treatments, such as indoxyl sulfate.

In some embodiments, the methods disclosed herein reduce a concentration of one or more uremic toxins or precursors thereof in a part of the patient's GI tract, e.g., the patient's colon. In some embodiments, the methods disclosed herein reduce a concentration of one or more uremic toxins or precursors thereof in the patient's bloodstream. In some embodiments, the methods disclosed herein reduce a concentration of indoxyl sulfate in the patient bloodstream by reducing a concentration of tryptophan or indole in the patient's digestive system (e.g, colon).

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

Example 1

Formation of $Ca^{2+}$ Alginate Spheres

This example demonstrates the formation of exemplary particles (polymeric spheres) by a method generally referred to as "spherification". It consists of formation of a droplet of a dilute (<5%) but viscous solution of $Na^+$ alginate in water or buffer, followed by transferring one or more droplets of the alginate solution into a solution containing free $Ca^{++}$ ions (such as $CaCl_2$). The $Ca^{++}$ ions diffuse into the alginate solution, and complex with the carboxylate groups on the alginate polymer chains, resulting in condensation and crosslinking of the alginate into a gel. The gelation occurs initially at the outer surface of the alginate droplet, producing a gelled "shell" around the fluid inner core of alginate. As incubation of the particle in the $Ca^{++}$ solution continues, the $Ca^{++}$ ions diffuse further through the gelled cortex into the core alginate solution within; the gelation proceeds inward into the bead interior until the entire alginate mass is in gel form, and the bead is a solid continuous gel. Important variables are the concentrations of the alginate and $Ca^{++}$ solutions, the volume of the alginate droplets, the total volume of the $Ca^{++}$ solution into which the alginate droplet in injected the temperature, the pH, the duration of the incubation, and the presence of any other solutes in either solution.

Addition of the droplet alginate solution into to the $Ca^{++}$ solution is usually accomplished by forming a drop of alginate solution on an orifice in a conical object like a pipette tip. In general, the desired alginate droplet size is between 1 and 5 mm in diameter; since the intended route of delivery to the human GI tract is via ingestion, a much larger diameter would be impractical for those applications; however, for research purposes and animal testing, diameters outside this range can be desirable. This can be done by varying the size of the orifice from which the drop of alginate falls into the $Ca^{++}$ solution.

Fabrication

Figure 3:
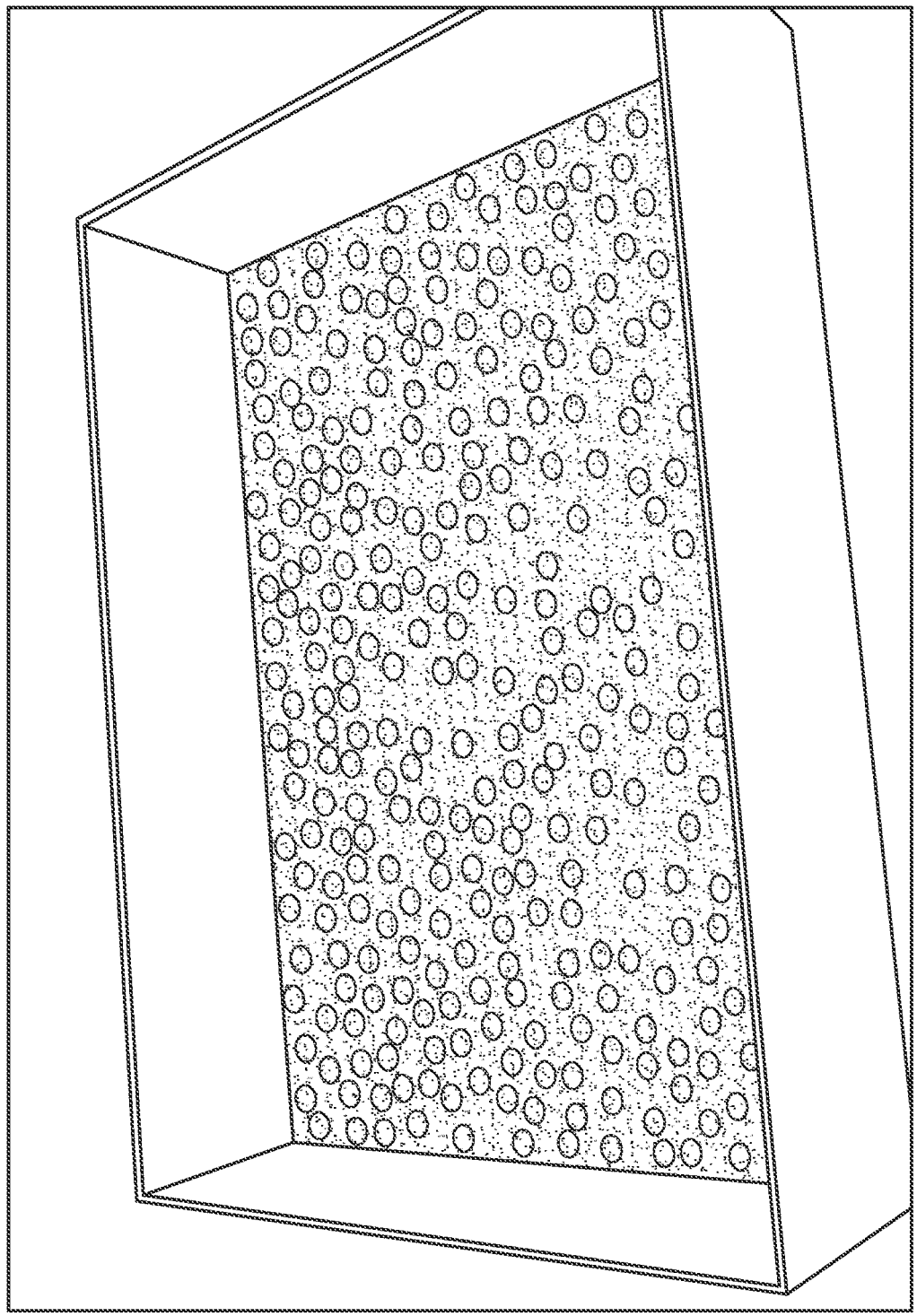
FIG. 3 is a photograph of exemplary $Ca^{++}$ alginate beads (~3 mm in diameter) formed by the process described herein using a commercial 96-droplet former.
Figure 4:
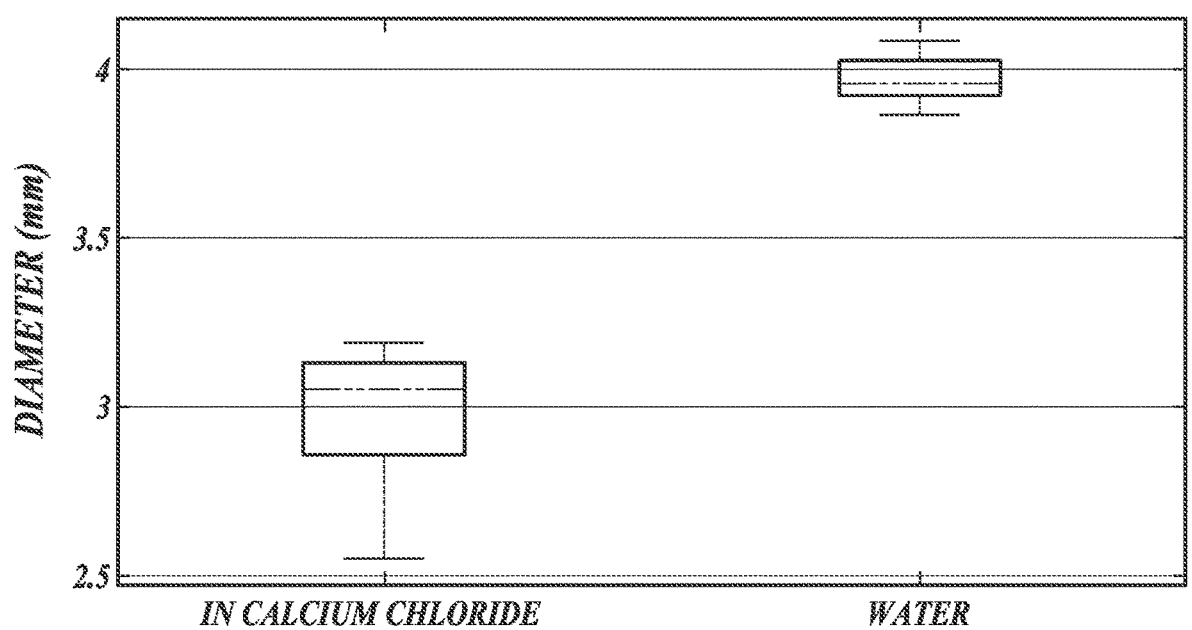
FIG. 4 demonstrates the effect on size of storage of exemplary alginate beads over a 3-week period in either the $CaCl_2$ solution in which they were formed, or in water.

For use in production of edible alginate spheres, commercial manufacturers have produced drop-forming tools that produce 96 droplets at a time. Such commercial apparatus has been used to form spheres shown in FIG. 3. Droplets formed in this way can be stored in the refrigerator for at least 3 weeks with little change if they are stored in the $CaCl_2$ solution in which they were formed but tend to swell if they are stored in distilled water, as shown in FIG. 4.

Figure 5C:
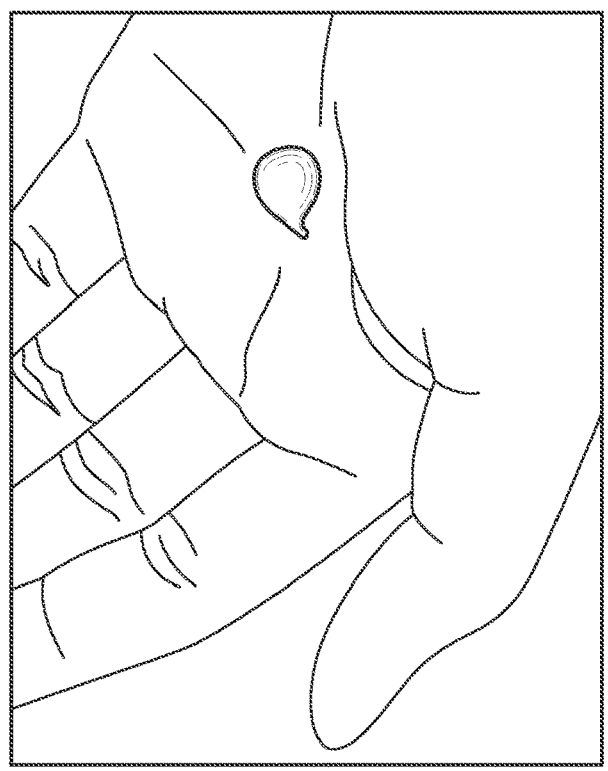
FIGS. 5A-C show pipetting equipment used to form exemplary calcium alginate beads for work described in this document and beads produced by the equipment. The alginate solutions were dropped from the commercial pipettor into the $CaCl_2$ solution below (5A).
Figure 5B:
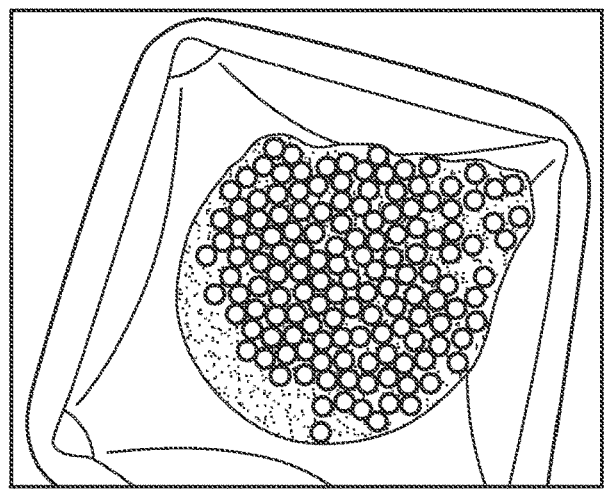
Figure 5A:
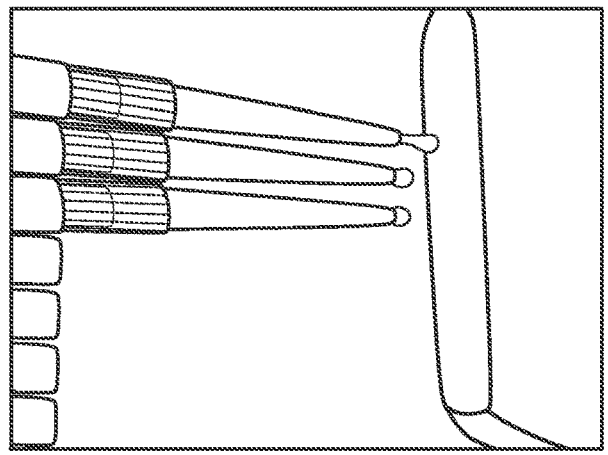

Other sphere-forming methods using laboratory equipment can be as fast and are easier to re-use. FIGS. 5A and 5B show the equipment used for further work in the lab described below. Alginate solutions of various concentrations were aspirated into a multichannel pipet (Rainin E4XLS), after which 50 μl/aliquots were dropped into $CaCl_2$ (0.5-1%).

The size of beads was measured using several techniques, including two fluorescence-based techniques. The beads were imaged in fluorescence mode using a gel imager (BioRad) under ultraviolet or blue excitation, the bead size in pixels was measured, and the corresponding size in mm was calculated. Second, the beads were imaged with an inverted fluorescence microscope (Zeiss Axiovert 25 inverted fluorescence microscope) with a bandpass filter set for fluorescein and Texas Red™ fluorophores (Excitation: Dual-bandpass 479/585 nm (Semrock FF01-479/585); Emission: Dual bandpass 524/628 nm (Semrock FF01-524/628); Dichroic: Dual-edge 505/606 nm (Semrock FF505/606-Di01)). The size of imaged beads was correlated with a microscopy standard (Applied Micro SM-3). Both measurements demonstrated that bead sizes were initially about 3 mm in diameter.

Example 2

Tryptophan Removal from Buffer by BSA/Hydrogel Particles

This example demonstrates the removal of a precursor of a uremic toxin using an exemplary hydrogel particle comprising a molecular binder/adsorbent immobilized within the particles. One of the key uremic toxins is indoxyl sulfate, which is produced in the liver as a breakdown product of indole. Indole, in turn, is produced as product of microbial metabolism of the amino acid L-tryptophan in the gut by the gut microbiome. L-tryptophan, as well as the other three aromatic L-amino acids, are known to bind strongly to albumin, and is transported in plasma by albumin in the same site that carries indoxyl sulfate. Removal of tryptophan from the gut is believed to reduce the production of indole in the gut, thus reducing the downstream production of indoxyl sulfate, and thereby reducing the levels of indoxyl sulfate in the blood. A model system of removal of indole from the gut was developed to demonstrate that the exemplary hydrogel particles loaded with albumin can survive a trip through the GI tract and also can remove tryptophan from a model solution, i.e., intestinal contents. Described below is proof-of-principle of the method for removing albumin-binding toxins using an exemplary composition comprising bovine serum album encapsulated in alginate beads.

Fabrication

Preparation of Alginate Beads Incorporating Bovine Serum Albumin

Sodium Alginate of varying concentrations (1.0, 1.5, 2.0%) were first prepared by dissolving in 50 mM Tris pH 8.0 buffer. BSA (Gemini Bioproducts 30% stock solution Cat #700-110) at 1 mM was added to the mix under continuous stirring. The mixture was then degassed to remove air bubbles. The BSA-alginate mix was aspirated into a multi-pipet (Rainin E4XLS), and 50 μl/aliquots were dropped into $CaCl_2$ (0.5-1%). BSA encapsulated in alginate hydrogel was washed with buffer and stored at 4° C. until use. FIG. 3 shows the process of making BSA encapsulated alginate hydrogel beads. The beads were approximately 3 mm in diameter. Control beads without BSA were generated similarly.

BSA-alginate hydrogel can be generated either firm with no inner liquid by incubating in $CaCl_2$ for at least 40 minutes, or with an inner liquid core by removing the beads from $CaCl_2$ within 10-15 minutes. The firmness of the hydrogel also varies with the different percentage of the sodium alginate with increasing firmness at increasing concentrations.

Figure 6A:
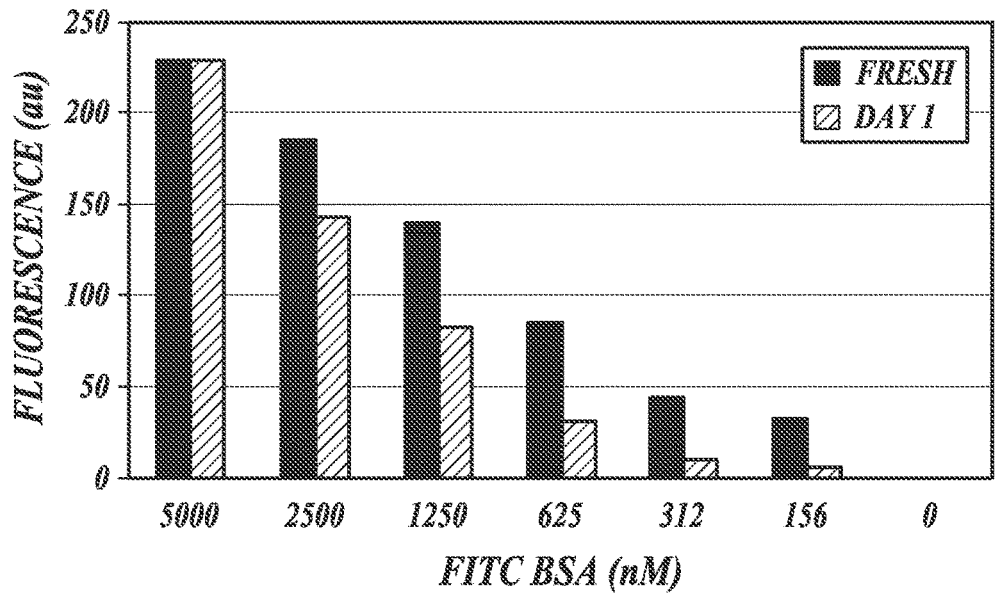
FIG. 6A is a graph of fluorescence of $Ca^{++}$ alginate (1%) beads made with 2.25 mM BSA+ spiked in FITC-BSA in 50 mM Tris buffer pH ~8.0 (left).
Figure 6B:
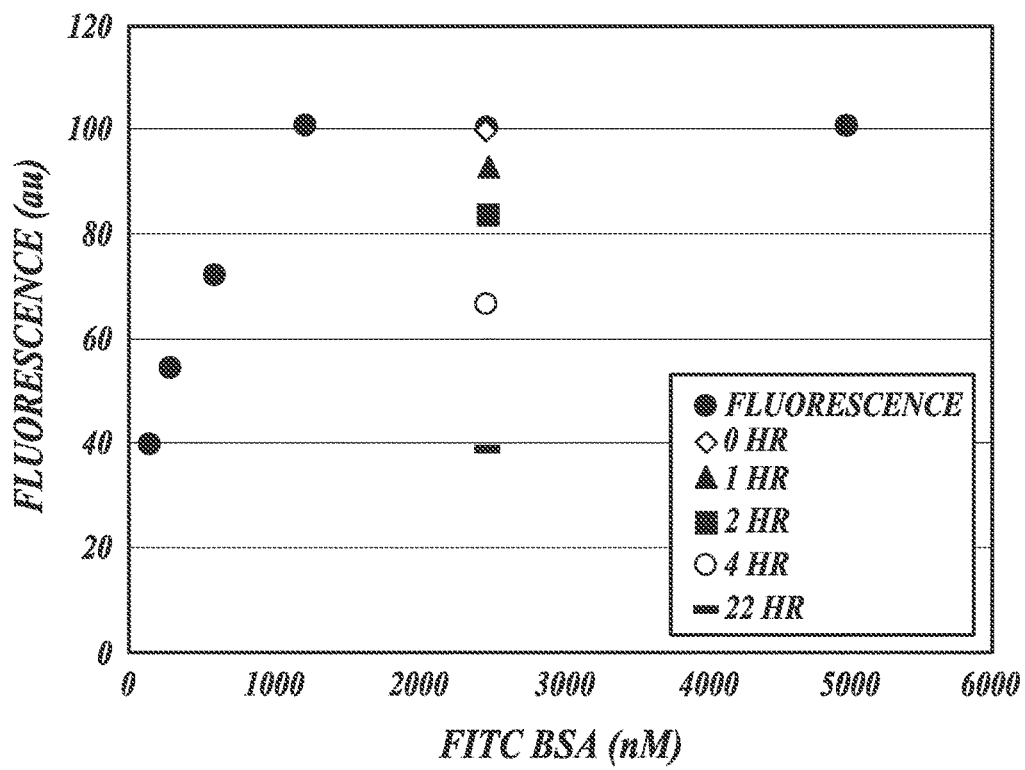
FIG. 6B demonstrates the loss of FITC-BSA from the beads at 2.5 µM over time. Note that by even one day of storage in $Ca^{++}$-free buffer, there was evidence of substantial escape by BSA from the beads.

Initial experiments using fluorescently-labeled BSA indicated that BSA could escape from the less-tightly crosslinked alginate beads over a short storage period as shown in FIG. 6. Evidently the gels formed at these concentrations are insufficiently tight to immobilize proteins the size of BSA. Therefore, an approach was developed to prevent mobility of uremic toxin adsorbents such as proteins (e.g., BSA) after they had been encapsulated in the alginate bead.

Crosslinking BSA Encapsulated Alginate Bead to Prevent BSA Leakage

Glutaraldehyde is a divalent aldehyde that readily forms covalent bonds with two different primary amine groups and has long been used to form gels of proteins through intermolecular covalent bond formation. When excessive treatment is avoided (that might affect active sites), enzymes and other proteins can remain functional after formation of aldehyde-crosslinked gels consisting entirely of solutions of the proteins. As there are no amine groups in the alginate itself, the chemical action of glutaraldehyde on a protein-containing alginate bead should be restricted to crosslinking of amines on the proteins encapsulated in the hydrogel.

Figure 7B:
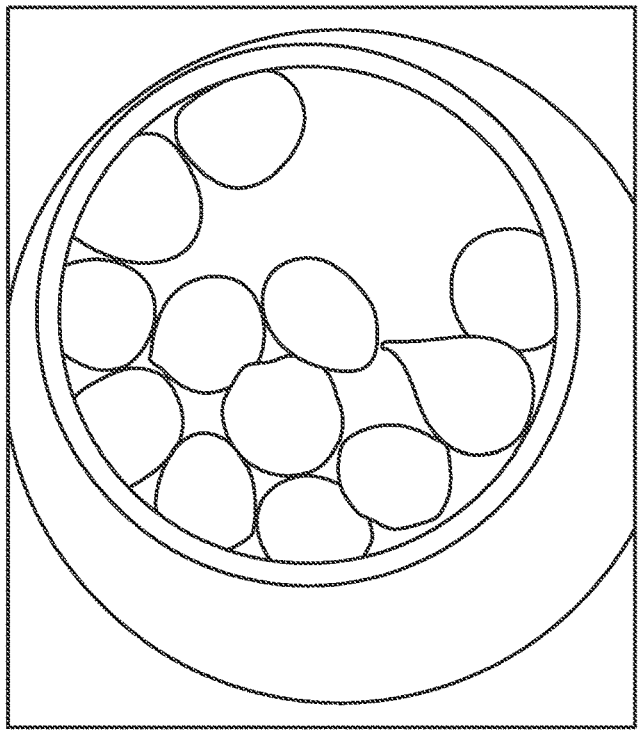
FIG. 7A-B are images of untreated (7A) and glutaraldehyde-treated (7B) exemplary BSA-alginate beads. The treated beads appeared to have a "halo" around the surface, perhaps indicating condensation of the gel caused by the crosslinking of the albumin.
Figure 7A:
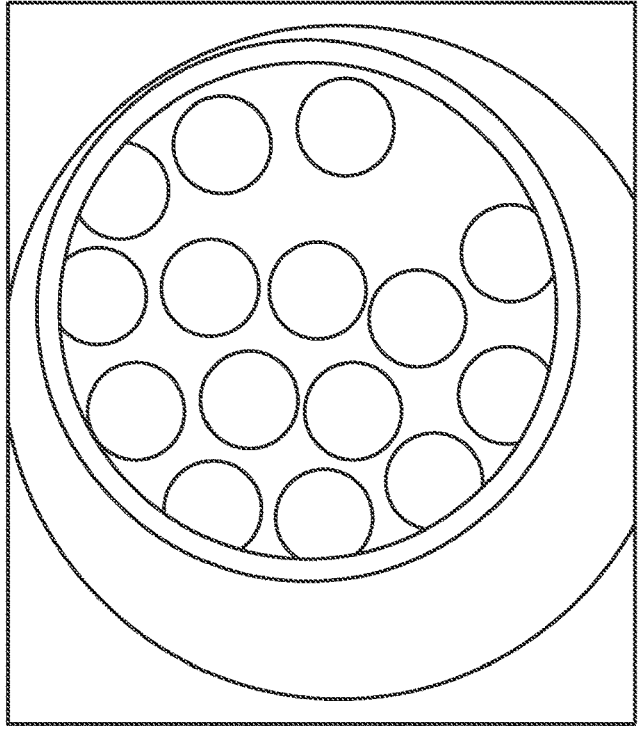

BSA-alginate (1 mM BSA, 1.5% calcium alginate) hydrogel beads (prepared by the above procedure) were treated with 0.3% glutaraldehyde prepared in 0.9% saline solution for 6 minutes. The glutaraldehyde treatment was stopped using 100 mM Tris pH 8.0 buffer, and the beads were then washed with 50 mM Tris pH.8 buffer. The results are shown in FIGS. 7A and 7B.

Figure 8:
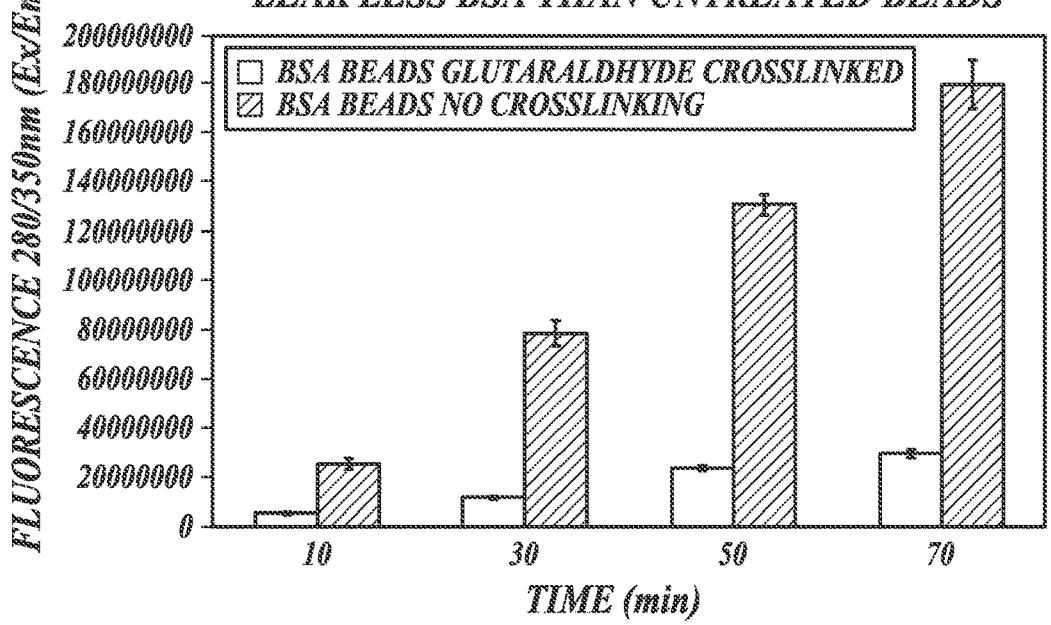
FIG. 8 demonstrates BSA leakage from exemplary untreated and glutaraldehyde-treated BSA-alginate hydrogel beads, showing that that beads in which the BSA has been crosslinked leak much less BSA.

The untreated and glutaraldehyde-treated BSA-alginate beads were tested for BSA leakage. Approximately 15 beads from each set were incubated with 1 ml of Tris pH 8.0 buffer in a well plate at 37° C. The buffer from the wells was periodically removed and added to a black well plate and read in a plate reader. The fluorescence of the indole ring in the tryptophan inherently present in the BSA was assayed at 280/350 nm (Excitation/Emission). This treatment with glutaraldehyde is important because any leakage of BSA would contribute to the tryptophan being measured in the section described below. FIG. 8 shows that this particular protocol of glutaraldehyde crosslinking prevented BSA escape from the hydrogel to a significant degree compared to untreated BSA hydrogel beads. Additional glutaraldehyde treatment may further prevent protein loss.

Absorption of Tryptophan by BSA Encapsulated Alginate Hydrogel

Figure 9:
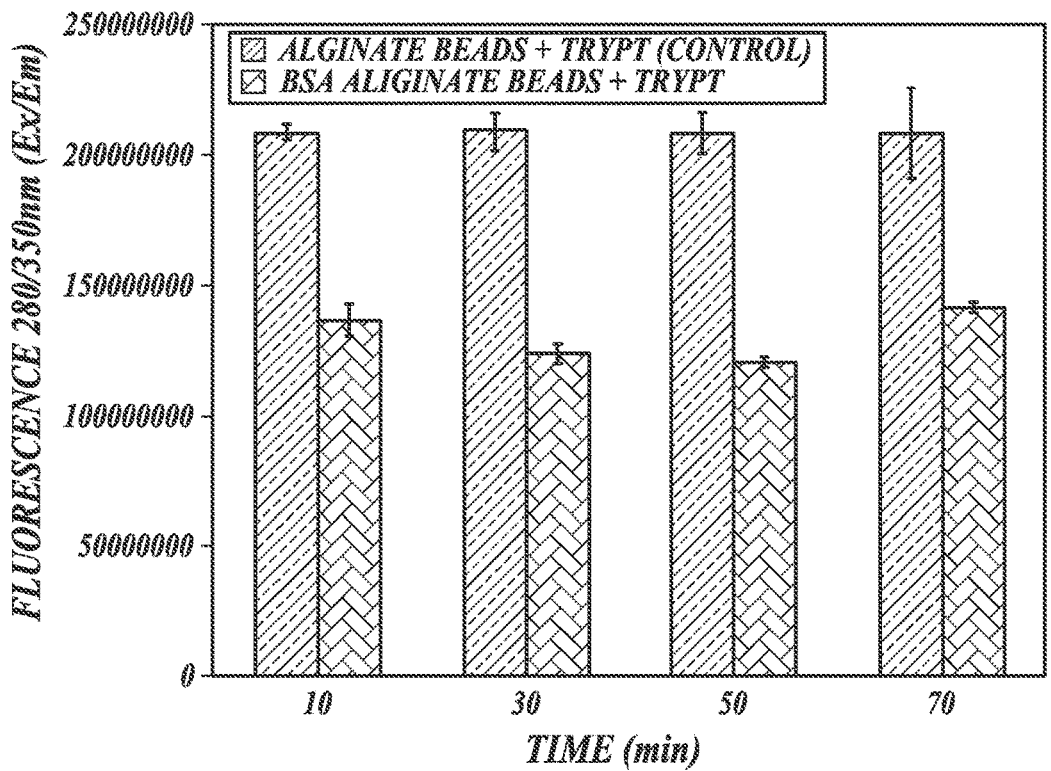
FIG. 9 is a demonstration of absorption of tryptophan by exemplary crosslinked BSA-alginate bead. Alginate beads were used as controls. Note the substantially larger drop in solution tryptophan concentration when the solution contains added BSA-alginate beads, as compared to the control BSA-free alginate beads.

Exemplary BSA-alginate beads (1 mM BSA, 1.5% alginate) and alginate-only beads (1.5% alginate) were treated with glutaraldehyde as described in the previous section. After stopping the glutaraldehyde reaction and the washes, 1 ml of 0.5 mM tryptophan in Tris pH 8.0 buffer was added to 15 beads in each well plate and incubated at 37° C. The buffer outside the beads was periodically assayed for tryptophan by reading fluorescence at 280/350 nm (Excitation/Emission). FIG. 9 shows the absorption of tryptophan by BSA-encapsulated alginate beads. In comparison, in the control with alginate beads only, the tryptophan concentration remained higher than in the presence of the BSA alginate beads.

Effect of pH on the BSA-Alginate Beads

Figure 10B:
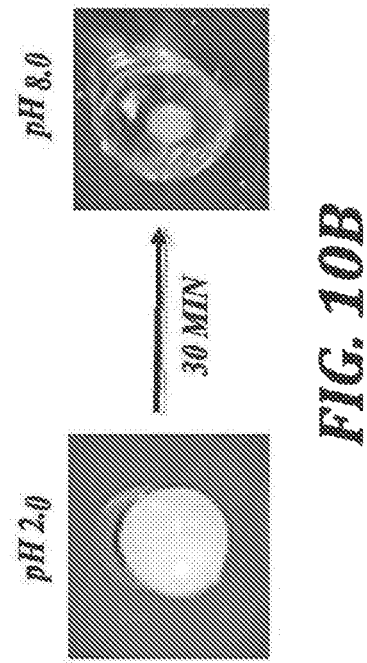
FIGS. 10A-B shows effect of pH on exemplary BSA alginate beads. At pH 2.0 BSA alginate beads turn white and shrink to half their diameter, in contrast to beads in pH 8.0 and 9.0, which remain transparent (10A). B. when beads equilibrated at pH 2.0 are shifted back to pH 8.0, they revert to a transparent state, and their original diameter (10B).
Figure 10A:
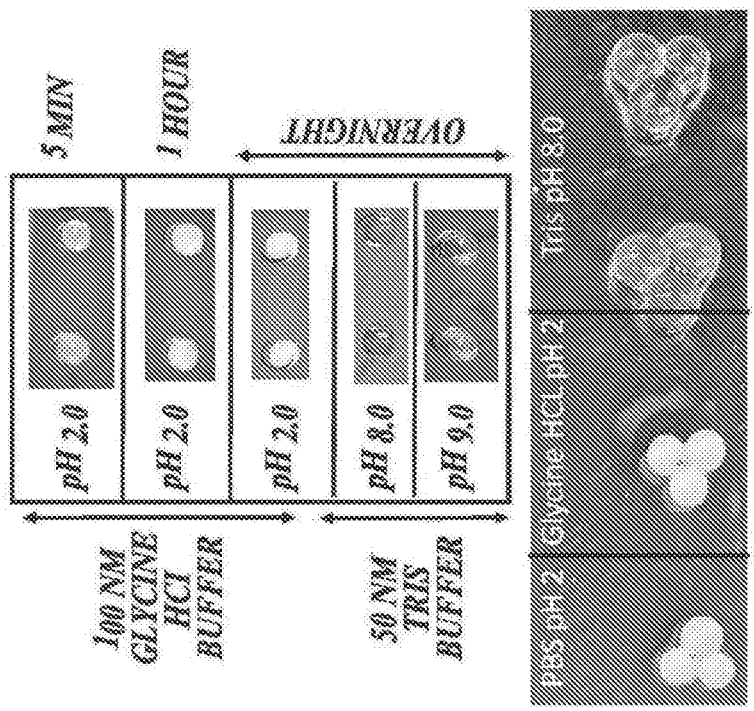

As a first step in determining the effect of transit through the GI tract on the survival of the exemplary BSA-loaded alginate beads, the effect of pH on the BSA alginate beads was tested to simulate the changes that would take place as the beads would travel from the mouth to the colon. A pH 2.0 buffer was chosen for the gastric condition and pH 8.0 and 9.0 for the conditions in the small intestine. Exemplary BSA alginate beads were added to glycine-HCl buffer at pH 2.0 or to PBS buffer adjusted to pH 2.0 and imaged over a time period. Within an hour, BSA alginate beads not only turned white but also shrank in size by half (FIG. 10A). In contrast, the beads subjected to pH 8.0 and 9.0 remained transparent and unchanged in size. When the beads were transferred from pH 2.0 buffer back to Tris buffer at pH 8.0, they reverted to the original transparent state within 30 minutes (FIG. 10B). BSA changes its conformation with changes in pH. This example demonstrates that while BSA will be subjected to different pH through the digestive tract, no matter how well the gel beads are buffered, the reversal in conformational change can render the entrapped BSA active again as the beads travel from the acidic stomach environment to the small intestine and colon.

Example 3

Encapsulation of Live Bacteria into Alginate Beads and their Survival in Varying pH Environments Materials and Methods:

Growth and washing of bacterial cells. *E. coli* K12 (ATCC 10798) was streaked from freezer stock onto LB-agar plate (Amresco J104, VWR, West Chester, PA, USA) After plate had been incubated at 37° C. for at least 16 hours, a single colony was picked and inoculated into 2-3 ml LB broth (Amresco J106, VWR) in a 27 ml loose-capped glass tube. Inoculated broth was grown overnight at 37° C., shaking at 250 rpm. Cells were subcultured 1:100 into 15 ml fresh LB broth and grown as above for approximately 2 hours ($OD_{600}$=0.8 to 2.0). Cells were recovered by centrifugation (2 minutes at 12,000×g in 1 ml aliquots, 1.5 ml microfuge tubes), resuspended in 1 volume saline (Tris or unbuffered as noted) and recovered again. After the second wash and recovery, cells were resuspended in 0.1-0.25 volumes saline (Tris or unbuffered as noted).

Minimal indicator medium contained the following components (expressed as g/L): $K_2HPO_4$ (0.3), NaCl (0.5), $NH_4Cl$ (1), glucose (10), $MgSO_4$ (0.5), $CaCl_2$ (0.015), bromothymol blue (0.03). The pH of this medium was not adjusted but measured at 7.0 when tested.

Heat-killing of bacterial cells. If a dead *E. coli* control was performed, at this point a fraction of the washed cells were removed to a separate 1.5 ml microfuge tube. This tube was placed on a 95° C. heat block for 10-15 minutes before removal. Heat killing of cells was confirmed by plating 50-100 μl of the heated mixture onto LB Agar.

Formation of *E. coli* beads. Cells were diluted into saline (Tris or unbuffered as noted), then sodium alginate was added to a final concentration of 2% (w/v). Cell concentrations in this alginate solution of less than or equal to $OD_{600}$=0.5 (roughly $4 \times 10^8$ cells/ml) had the best structural integrity in our hands. After alginate was dissolved (at least 10 minutes), solution was dropped into at least 10 ml 2% $CaCl_2$ (w/v) in a wide-mouthed sterile container using a 1000 μl pipette tip from which the lower 5 mm had been removed aseptically. This resulted in beads with an average diameter of 4 mm (or an average volume of approximately 33.5 μl). Beads were incubated in the $CaCl_2$ solution for at least 30 minutes (unless noted) before being aseptically removed to a new sterile tube and overlaid with saline (Tris or unbuffered to match the alginate solution used to make the beads).

Glucose depletion medium contained the following components (expressed as g/L): $K_2HPO_4$ (0.3), NaCl (0.5), $NH_4Cl$ (1), glucose (4), $MgSO_4$ (0.5), $CaCl_2$ (0.015) Live/Dead staining. To assess *E. coli* cell viability after incorporation into calcium alginate beads, a live/dead stain kit was used (Invitrogen LIVE/DEAD™ BacLight™ Bacterial Viability Kit, for microscopy & quantitative assays, ThermoFisher L7012). The kit contains two dyes: propidium iodide and SYTO 9. These two dyes were mixed at a 1:1 ratio. Then the mixture was diluted (1:100 or 1:200 as noted) in saline (Tris- or un-buffered as noted) and then applied to the bead (20-40 μl per bead). After allowing to soak for 30 minutes, beads were cut with a clean razor blade, and the cut surface placed down onto a glass microscope slide. Beads were imaged using an Axiovert inverted microscope (Zeiss Axiovert 25) using a color camera (Retiga 1300i) and a filter set for the appropriate fluorescence wavelengths (Dual-bandpass 479/585 nm excitation (Semrock FF01-479/585) and 524/628 nm emission (Semrock FF01-524/628) filters).

Measurement of glucose concentration. A CVS Health Advanced Glucose Meter (AgaMatrix, Inc., Salem, NH, USA) was used to measure the glucose concentration of solutions. A compatible test strip was inserted into a machine, and then 2 μl of fluid was applied to the end of the test strip. Glucose is reported in mg/dL. Solutions were measured in duplicate at each time point and the mean results are reported.

Figure 11:
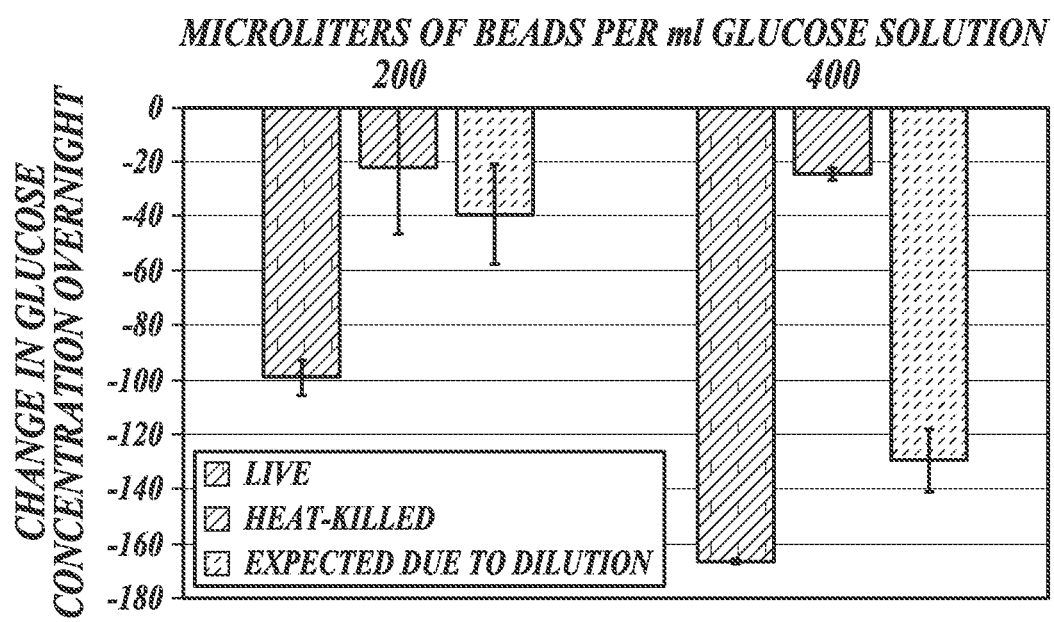
FIG. 11 demonstrates removal of glucose from buffer by exemplary beads comprising bacteria. Beads containing live

Experiment #1-*E. coli*-Laden Beads can Deplete the Surrounding Medium of a Small Molecule at Physiological Temperature Beads were made as described above containing either live or heat-killed *E. coli* cells. Six beads (approximately 200 µl total volume) were added to either 1 ml or 0.5 ml glucose depletion medium in a 10 ml sterile capped glass test tube. Glucose was measured at this initial T=0 time point. Tubes were incubated at 37° C., shaking at 250 rpm. After 19 hours incubation, glucose was measured again (FIG. 11).

Beads containing both live and heat-killed *E. coli* caused an apparent reduction of glucose in the surrounding solution over the course of 19 hours. The reduction seen in the heat-killed condition appears to be minimal and is not significant for the 200 µl beads/ml condition. The reduction appears to be dose-dependent and in heat-killed cell-laden beads might be due to diffusion of glucose into the (not sampled) bead volume. If a delayed dilution due to diffusion effect occurred, and the entire volume of the bead was accessible to glucose diffusion (aqueous), more drastic reductions in glucose concentration would be expected. The retention of glucose in the buffer outside heat-killed *E. coli*-laden beads supported the hypothesis that a large portion of the bead volume is not accessible to glucose via diffusion. As the beads were denser than saline (they settle out of solution quickly), this suggests that a relatively large fraction of their volume is calcium alginate polymer and not water.

When beads containing live *E. coli* were used, more glucose was removed from solution than could be explained by dilution. This result supports the hypothesis that the *E. coli* cells inside the polymer matrix are capable of small molecule uptake, and are metabolically active.

Experiment #2-*E. coli*-Laden Beads Produce Acid (an Indicator of Metabolism) Under Physiological Conditions Beads containing *E. coli* l(live or heat-killed) were placed into minimal indicator medium (described above) and incubated at 37° C., shaking at 250 rpm, overnight. During this time, *E. coli* cells free in solution turned this indicator medium yellow, dropping the pH to approximately 4.5 (from 7.0). Beads containing live *E. coli* showed this same shift in pH, although cells were almost entirely contained within the bead (optical density of the extra-bead medium was unchanged, though some live cells were found when this medium was plated). Beads containing heat-killed *E. coli* or made without the incorporation of bacterium did not show this same shift in pH.

As these cells were grown with vigorous shaking under aerobic conditions, the majority of the energy conservation done by *E. coli* in these beads is via aerobic respiration (glycolysis and the TCA cycle). This process generates $CO_2$ which can acidify water by forming carbonic acid. *E. coli* can also ferment glucose to mixed acids (lactate, acetate, succinate, and formate) and gas, but this fermentation only happens in the absence of oxygen, as can occur at greater bead depths.

Experiment #3-*E. coli* Cells Largely Survive the Bead Making Process, as Visualized by Live/Dead Staining, but are Challenged by Extended Exposure to Low pH

*E. coli* beads were made with live or heat-killed cells washed and diluted in either saline (0.9% NaCl), 10 mM Tris-buffered saline (pH 7.4) or 100 mM Tris-buffered saline (pH 7.4). Live beads were incubated in 100 mM glycine-HCl buffer (pH 2) for 5, 30, or 60 minutes while shaking at 37° C. After low-pH incubation, beads were neutralized with 1 mL 100 mM Tris-buffered saline (pH 7.4) for at least 30 minutes. Beads were then stained with live/dead stain and visualized as described above. Green staining indicated live cells, while red staining indicates dead cells. The results are summarized in Table 1 below.

Table 1: *E. coli* encapsulated in calcium alginate beads subjected to low pH (100 mM Glycine-HCl, pH 2.0) in the presence of different amounts of buffer within the beads. Cells were stained with BacLight LIVE/DEAD stain and imaged. Live or dead determination was done by eye, based on the dominant color of the emitted fluorescence. Beads that showed green color were determined to contain live *E. coli*, while those showing red were determined to be dead. Beads that were made with 100 mM Tris-buffered saline were predominantly yellow in color, indicating death of some of the cells but not others, due to the protective effect of a higher buffer concentration.

TABLE 1

| Tris Buffer (nM) | Heat-killed | Live (no low pH treatment) | 5 min treatment | 30 min treatment | 60 min treatment |
|---|---|---|---|---|---|
| 0 | Dead | Live | Live | Dead | Dead |
| 10 | Dead | Live | Live | Dead | Dead |
| 100 | Dead | Live | Live | Partially live | Dead |

Short exposure to a low pH, such as that encountered in the human stomach, did not result in widespread *E. coli* cell death. However, longer exposures of 30 and 60 minutes did result in red staining, indicating cell death. Cultures grown using unstained beads prepared in parallel confirmed that live cells did not remain alive in these beads after 30 minutes of low pH treatment. However, buffering the medium inside the gel bead had a protective effect. *E. coli* in beads made with 10 mM or 100 mM Tris-buffered saline survived the 5-minute low pH treatment, but those prepared using unbuffered saline did not. A further experiment showed that *E. coli* in beads made with 50 mM Tris-buffered saline did not survive a 15-minute low-pH treatment. However, Tris buffer can easily diffuse out of the gel bead. The effects of low pH can be mitigated by inclusion of a buffer that does not diffuse out of the bead during the bead's passage through the stomach, for example, a high molecular weight polymer with titratable groups. In some embodiments, a protein such as albumin or another inert protein, can be included as a buffering agent.

While illustrative embodiments have been illustrated and described, it will be appreciated that various changes can be made therein without departing from the spirit and scope of the invention.

The embodiments of the invention in which an exclusive property or privilege is claimed are defined as follows:

1. A composition for reducing concentration of one or more uremic toxins or uremic toxin precursors in a patient's digestive system, the composition comprising a plurality of hydrogel particles, each particle comprising an agent encapsulated and retained within the particle and capable of reducing a local concentration of one or more uremic toxins or uremic toxin precursors;
   wherein the hydrogel particles comprise a shell and a core,
   wherein the core comprises one or more agents disposed within one or more indigestible hydrogel spheres,
   wherein the shell allows diffusion of uremic toxin into the core, and
   wherein the composition further comprises a fluid carrier containing the plurality of hydrogel particles.

2. The composition of claim 1, wherein the agent adsorbs or absorbs one or more uremic toxins or uremic toxin precursors.

3. The composition of claim 1, wherein the agent is a protein.

4. The composition of claim 3, wherein the protein is bovine serum albumin (BSA).

5. The composition of claim 3, wherein the one or more uremic toxins or uremic toxin precursors is tryptophan or indole.

6. The composition of claim 1, wherein the hydrogel particles comprise spherical hydrogel particles.

7. The composition of claim 6, wherein the spherical hydrogel particles have a diameter from about 1 mm to about 10 mm.

8. The composition of claim 1, wherein the hydrogel is non-toxic to a mammal before or after exposure to the conditions of the GI tract.

9. The composition of claim 1, wherein the hydrogel is indigestible by a human.

10. The composition of claim 1, wherein the hydrogel comprises a polyethylene glycol (PEG) hydrogel.

11. The composition of claim 3, wherein the protein is covalently crosslinked after encapsulation in the hydrogel.

12. The composition of claim 1, wherein the plurality of hydrogel particles comprises more than one type of hydrogel particles, wherein each type of hydrogel particles is capable of removing a different uremic toxin and the types of hydrogel particles are distinguished by the particles' materials, sizes, shapes, architecture, agents encapsulated within the particles, colors, or a combination thereof.

13. The composition of claim 1, wherein the composition further comprises hydrogel particles comprising activated charcoal.

14. The composition of claim 1, wherein the fluid carrier comprises one or more sweeteners, nutrients, flavoring agents, or a combination thereof.

* * * * *